US011678893B2

(12) United States Patent
Mahaffey

(10) Patent No.: US 11,678,893 B2
(45) Date of Patent: Jun. 20, 2023

(54) SYSTEMS FOR ADVANCING A PIN WIRE WITH A DRIVER DEVICE

(71) Applicant: Zimmer, Inc., Warsaw, IN (US)

(72) Inventor: Mark Mahaffey, New Philadelphia, OH (US)

(73) Assignee: Zimmer, Inc., Warsaw, IN (US)

( * ) Notice: Subject to any disclaimer, the term of this patent is extended or adjusted under 35 U.S.C. 154(b) by 893 days.

(21) Appl. No.: 16/481,285

(22) PCT Filed: Feb. 9, 2018

(86) PCT No.: PCT/US2018/017615
§ 371 (c)(1),
(2) Date: Jul. 26, 2019

(87) PCT Pub. No.: WO2018/148539
PCT Pub. Date: Aug. 16, 2018

(65) Prior Publication Data
US 2020/0038040 A1 Feb. 6, 2020

Related U.S. Application Data

(60) Provisional application No. 62/457,556, filed on Feb. 10, 2017.

(51) Int. Cl.
*A61B 17/16* (2006.01)
(52) U.S. Cl.
CPC ........ *A61B 17/1697* (2013.01); *A61B 17/162* (2013.01); *A61B 17/1631* (2013.01)
(58) Field of Classification Search
CPC .............. A61B 17/1697; A61B 17/162; A61B 17/1633; A61B 17/8897; A61B 17/8861
See application file for complete search history.

(56) References Cited

U.S. PATENT DOCUMENTS 4,091,880 A * 5/1978 Troutner ............ A61B 17/1628
173/217
5,482,038 A * 1/1996 Ruff ........................ A61B 5/296
600/372
(Continued)

FOREIGN PATENT DOCUMENTS

CN 1805717 A 7/2006
CN 110248612 9/2019
(Continued)

OTHER PUBLICATIONS

"European Application Serial No. 18708004.9, Response to Communication pursuant to Rules 161(1) and 162 EPC filed Apr. 6, 2020", 26 pages.
(Continued)

*Primary Examiner* — Matthew J Lawson
(74) *Attorney, Agent, or Firm* — Schwegman Lundberg & Woessner, P.A.

(57) ABSTRACT

An engagement mechanism for a driver instrument (24) can comprise a mobile shaft (121, 221), a collet (122, 222) and an angled engagement interface (124; 136A-D). The mobile shaft comprises a first shaft portion (128, 228) located at a proximal end of ON the mobile shaft, a driver portion (126, 226) located at a distal end of the mobile shaft, and an internal passageway (180, 280) extending from the proximal end to the distal end. The collet comprises a second shaft portion (134, 234) disposed within the passageway at co the first shaft portion, and flexible arms (132A-D, 232A-D) extending from the second shaft portion within the driver portion. The angled engagement interface is positioned between the driver portion and the flexible arms, and is configured to permit the driver portion to push or deflect the flexible arms radially inward when the first shaft portion is slid along the second shaft portion. The angled engagement
(Continued)

interface can include bearings (224A-D) and a frusto-conical contact surface (124; 282A-D).

28 Claims, 14 Drawing Sheets

(56) References Cited

U.S. PATENT DOCUMENTS

| | | | |
|---|---|---|---|
| 5,747,953 | A | 5/1998 | Philipp |
| 5,794,715 | A | 8/1998 | Norman |
| 5,833,246 | A | 11/1998 | Trott |
| 5,902,306 | A | 5/1999 | Norman |
| 5,941,891 | A | 8/1999 | Walen |
| 5,961,532 | A | 10/1999 | Finley et al. |
| 5,993,454 | A | 11/1999 | Longo |
| 6,017,354 | A | 1/2000 | Culp et al. |
| 6,042,585 | A | 3/2000 | Norman |
| 6,045,564 | A | 4/2000 | Walen |
| 6,050,989 | A | 4/2000 | Fox et al. |
| 6,090,123 | A | 7/2000 | Culp et al. |
| 6,139,228 | A | 10/2000 | Longo |
| 6,202,760 | B1 * | 3/2001 | Lin ............... B24B 23/022 173/132 |
| 6,520,969 | B2 | 2/2003 | Lambrecht et al. |
| 6,675,910 | B1 * | 1/2004 | Lin ............... B24B 27/02 173/132 |
| 6,736,829 | B1 | 5/2004 | Li et al. |
| 6,752,816 | B2 | 6/2004 | Culp et al. |
| 6,786,897 | B2 | 9/2004 | McIe et al. |
| 6,917,183 | B2 | 7/2005 | Barlev et al. |
| 6,958,071 | B2 | 10/2005 | Carusillo et al. |
| 6,960,894 | B2 | 11/2005 | Carusillo et al. |
| 7,041,120 | B2 | 5/2006 | Li et al. |
| 7,237,990 | B2 | 7/2007 | Deng |
| 7,422,594 | B2 | 9/2008 | Zander |
| RE40,681 | E | 3/2009 | Pitzen et al. |
| 7,501,190 | B2 | 3/2009 | Ise |
| 7,517,351 | B2 | 4/2009 | Culp et al. |
| 7,638,958 | B2 | 12/2009 | Philipp et al. |
| 7,682,333 | B2 | 3/2010 | Deng |
| 7,717,931 | B2 | 5/2010 | Himes |
| 7,981,114 | B2 | 7/2011 | Zander |
| 7,998,157 | B2 | 8/2011 | Culp et al. |
| 8,035,487 | B2 | 10/2011 | Malackowski |
| 8,137,370 | B2 | 3/2012 | Deng |
| 8,419,760 | B2 | 4/2013 | Wiebe, III |
| 8,500,769 | B2 | 8/2013 | Dong |
| 8,556,909 | B2 | 10/2013 | Giersch et al. |
| 8,709,014 | B2 | 4/2014 | Ammann |
| 8,734,449 | B2 | 5/2014 | Schmied et al. |
| 8,956,342 | B1 * | 2/2015 | Russo ............... A61B 17/1626 403/322.2 |
| 8,974,513 | B2 | 3/2015 | Ford et al. |
| 9,101,494 | B2 | 8/2015 | Milz et al. |
| 9,155,576 | B2 | 10/2015 | Knopfle et al. |
| 9,161,792 | B2 | 10/2015 | Forderer |
| 9,198,701 | B2 | 12/2015 | Prien et al. |
| 9,198,703 | B2 | 12/2015 | Giersch et al. |
| 9,220,534 | B2 | 12/2015 | Wieland et al. |
| 9,265,541 | B2 | 2/2016 | Wieland et al. |
| 10,159,495 | B1 * | 12/2018 | Lambert ............ A61B 17/1622 |
| 2008/0299514 | A1 * | 12/2008 | Mosimann ............ B23B 31/207 433/132 |
| 2011/0196380 | A1 | 8/2011 | Cremer et al. |
| 2014/0276949 | A1 * | 9/2014 | Staunton ............... A61B 34/76 606/130 |
| 2015/0351820 | A1 | 12/2015 | Straslicka et al. |
| 2017/0340374 | A1 * | 11/2017 | Xie ............... A61B 17/8897 |
| 2018/0185080 | A1 * | 7/2018 | Bosshard ............ A61B 17/8861 |
| 2019/0343568 | A1 * | 11/2019 | Childers ............ A61B 17/8861 |

FOREIGN PATENT DOCUMENTS

| | | |
|---|---|---|
| WO | WO-2016081604 A2 | 5/2016 |
| WO | WO-2018148539 A1 | 8/2018 |

OTHER PUBLICATIONS

"International Application Serial No. PCT/US2018/017615, International Search Report dated Jun. 4, 2018", 6 pgs.

"International Application Serial No. PCT/US2018/017615, Written Opinion dated Jun. 4, 2018", 6 pgs.

"Universal Power System—Maintain Efficiency with the Power of Modularity", Zimmer Biomet, (2016), 8 pgs.

"Chinese Application Serial No. 201880010167.2, Office Action dated Nov. 2, 2021", w/ English translation, 17 pgs.

"Chinese Application Serial No. 201880010167.2, Response filed Feb. 18, 2022 to Office Action dated Nov. 2, 2021", w/ English claims, 15 pgs.

"Chinese Application Serial No. 201880010167.2, Decision of Rejection dated Jun. 6, 2022", w/ English Translation, 12 pgs.

"Chinese Application Serial No. 201880010167.2, Response filed Aug. 19, 2022 to Decision of Rejection dated Jun. 6, 2022", w/ English claims, 16 pgs.

* cited by examiner

SYSTEMS FOR ADVANCING A PIN WIRE WITH A DRIVER DEVICE

CLAIM OF PRIORITY

This application is a U.S. National Stage Application under 35 U.S.C. 371 from International Application Serial No. PCT/US2018/017615, filed on Feb. 9, 2018, and published as WO 2018/148539 A1 on Aug. 16, 2018, which claims the benefit of U.S. Provisional Patent Application Ser. No. 62/457,556, filed on Feb. 10, 2017, the benefit of priority of each of which is claimed hereby, and each of which is incorporated by reference herein in its entirety.

TECHNICAL FIELD

This document pertains generally, but not by way of limitation, to medical devices for use in surgery, such as instruments used in orthopedic procedures. More particularly, this disclosure relates, but not by way of limitation, to surgical instruments for driving elongated pins or wires into bones and/or other structures.

BACKGROUND

When attaching pins and/or wires to a bone of a patient, medical professionals may need to perform drilling, tapping, and/or screwing steps. When performing these tasks, powered surgical instruments may be utilized for driving elongated pins and/or wires. Powered surgical instruments used for driving elongated pins and/or wires may typically comprise a hand piece that drives a cannulated shaft through which a pin or wire may be passed. A drive shaft of the powered surgical instrument receiving the pin and/or wire may rotate, which in-turn rotates the received pin and/or wire in order to advance the pin and/or wire extending from the drive shaft into a bone structure or other structure. While pins usually have larger diameters than wires, for purposes of this description, the term "pins" and "wires" may be considered interchangeable.

Examples of pin wire driver devices are described in U.S. Pub. No. 2015/0351820 to Straslicka et al and U.S. Pat. No. 6,042,585 to Nomian.

OVERVIEW

The present inventors have recognized, among other things, that a problem to be solved can include the desire to simplify the design of existing pin wire driver devices, such as by reducing the number of components in an attachment apparatus. Additionally, the present inventors have recognized that a problem to be solved can include reducing the potential for an attachment apparatus to become temporarily seized-up such that the surgeon or other personnel may need to perform corrective measures to release the attachment apparatus, such as by disassembling the device or subjecting the device to an impact.

The present subject matter can help provide a solution to various problems associated with attachment apparatuses for driver devices by providing a mobile shaft and a flexible collet that have an angled contact surface. More specifically, an attachment apparatus can comprise a mobile shaft having captured bearings that engage an angled surface of a pin wire collet.

In an example, the present subject matter can help provide a solution to this problem, such as by providing an engagement mechanism for a driver instrument. The engagement mechanism can comprise a mobile shaft, a collet, and an angled engagement interface. The mobile shaft can extend along an axis and can comprise a first shaft portion located at a proximal end of the mobile shaft, a driver portion located at a distal end of the mobile shaft, and an internal passageway extending from the proximal end to the distal end. The collet can couple to a drive input of the driver instrument and can comprise a second shaft portion disposed within the passageway at the first shaft portion, and flexible arms extending from the second shaft portion within the driver portion. The angled engagement interface can be located between the driver portion and the flexible arms, and can be configured to permit the driver portion to push the flexible arms radially inward when the first shaft portion is slid along the second shaft portion.

In another example, a driver instrument can comprise a body, a drive input, a collet, a mobile shaft, a plurality of bearings, and a handle mechanism. The body can have an interior. The drive input can be located at least partially within the interior. The collet can be coupled to the drive input. The collet can comprise flexible arms extending in an axial direction, and shoulder portions connected to distal ends of the flexible arms. The mobile shaft can be disposed at least partially concentrically around the collet. The mobile shaft can comprise a first shaft portion engaged with the collet, and a driver portion positioned at a distal end of the first shaft portion to surround the flexible arms. The plurality of bearings can be mounted to the driver portion to selectively contact the shoulder portions. The handle mechanism can be engageable with the first shaft portion of the mobile shaft to translate the mobile shaft along the collet to selectively engage the plurality of bearings with the shoulder portions.

In yet another example, a method of advancing a pin wire using a pin wire driver can comprise: inserting a pin wire into a lumen of the pin wire driver; pulling a handle to actuate an engagement mechanism of the pin wire driver; advancing a mobile shaft within the engagement mechanism with the handle; pushing bearings mounted to the mobile shaft axially forward; engaging the bearings with shoulder portions of a pin wire collet; pushing flexible arms connected to the shoulder portions radially inward with the bearings to clamp onto the pin wire; and advancing the pin wire.

This overview is intended to provide an overview of subject matter of the present patent application. It is not intended to provide an exclusive or exhaustive explanation of the invention. The detailed description is included to provide further information about the present patent application.

DETAILED DESCRIPTION

Figure 1:
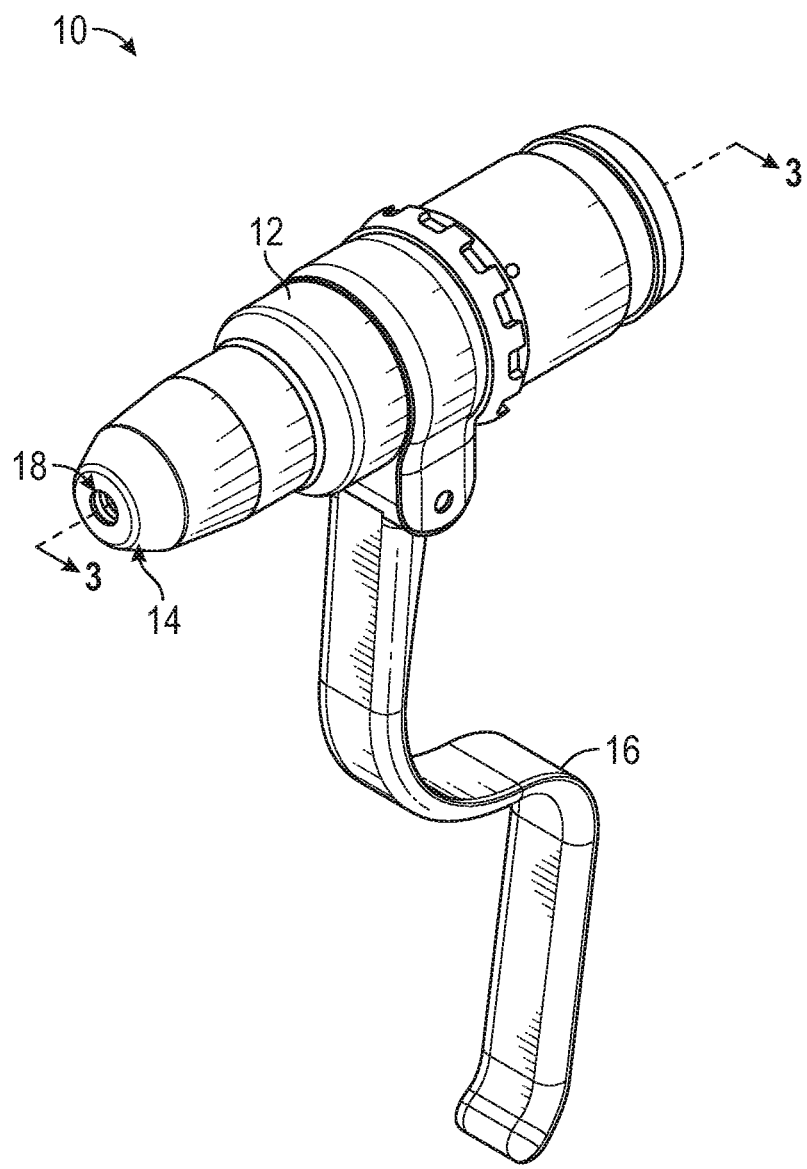
FIG. 1 is a schematic perspective view of an illustrative attachment apparatus for driving wires according to an aspect of the disclosure.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the proximal end (e.g., trailing end) of an object is the end that is closest to the individual or instrument inserting the object during a medical procedure and the distal end (e.g., leading end) of an object is the end that is farthest from the individual or instrument inserting the object during a medical procedure.

As used herein, any numerical or other order designations of elements (e.g., first, second, third, a, b, c, etc.) are used for descriptive purposes to improve the clarity of the description of the disclosure and differentiate between similar disclosed features. These numerical indications, unless expressly indicated, are not used for any limiting purposes.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

In some cases, pin wire driver attachments may facilitate driving and/or removing pins and wires by medical professionals during Total Knee Arthroplasty (TKA) procedures as well as other orthopedic or medical procedures and/or trauma. Some pin wire driver attachments may have variable grab points (e.g., grab points that may vary depending on pin or wire diameter), however, medical professionals appreciate a consistent grab point independent of wire size for consistency during procedures. Additionally, some pin wire driver attachments have a rotating outer nose, initial hold features set back a distance from the distal end of the pin wire driver attachment such that short pins (e.g., less than about 7-8 cm, or around 3 inches, may not receive an initial force applied thereto when received in the attachment), and manual adjustability to provide for various pin or wire diameters. As disclosed herein a pin wire driver attachment 10 (e.g., and instrument) may have a nose that does not rotate and does not require manual adjustment for various pin or wire 26 diameters. The pin wire driver attachment 10 may provide one or more consistent grab points independent of wire diameter, for example, a passive hold feature may engage a received pin or wire 26 at 1 mm, 2 mm, 5 mm, 7 mm, 9 mm, 11 mm, 13 mm, 15 mm, 20 mm, 25 mm, 35 mm, etc., at about 1 mm, 2 mm, 5 mm, 7 mm, 9 mm, 11 mm, 13 mm, 15 mm, 20 mm, 25 mm, 35 mm, etc. and/or between 0 mm and 50 mm, between 1 and 35 mm, between 5 mm and 30 mm, between 10 mm and 25 mm, 10 mm and 20 mm, 10 mm and 15 mm, etc., or other distance from a distal end of the pin wire driver attachment 10. In some instances, a first pin wire driver attachment may be configured for a first set of pins or wires 26 having a diameter within a first range (e.g., less than about 3 mm, between 0.6 mm and 2.2 mm, or other similar range) and a second pin wire driver attachment may be configured for a second set of pins or wires 26 having a diameter within a second range (e.g., greater than about 2.0 mm, between 2.0 mm and 4.0 mm, or other similar range). Other pin wire driver attachments 10 may be configured to facilitate use with pins or wires 26 having diameters falling in one or more other ranges that may overlap or may be entirely separate from than the specified ranges.

Turning to the Figures, FIGS. 1-5 depict various views of an illustrative apparatus or pin wire driver attachment 10 for use with a hand piece 22 in a pin wire driver 24, where the Figures are provided merely for the purpose of illustrating features disclosed herein. As discussed, medical professionals (e.g., surgeons, etc.) may use pin wire drivers 24 to drive and/or remove pins and/or wires 26 during TKA procedures, as well as during other orthopedic procedures and/or trauma situations, and/or during other medical procedures.

Referring to FIG. 1, the pin wire driver attachment 10 is depicted having a body 12, a nose 14 of the body 12, and a handle 16. The attachment 10 may be removably couplable to the hand piece 22. The handle 16, by itself or in combination with one or more features, may be an actuator or actuator member, which when adjusted may actuate one or more features at least partially within the body 12. The nose 14 may include an opening 18 in communication with a lumen 30 (see FIGS. 3A and 3B) extending at least partially through the body 12, where the opening 18 may extend through a distal end of the nose 14 to the lumen 30 extending at least partially through the body 12. In some cases, the lumen 30 may extend entirely through the body 12.

Figure 2:
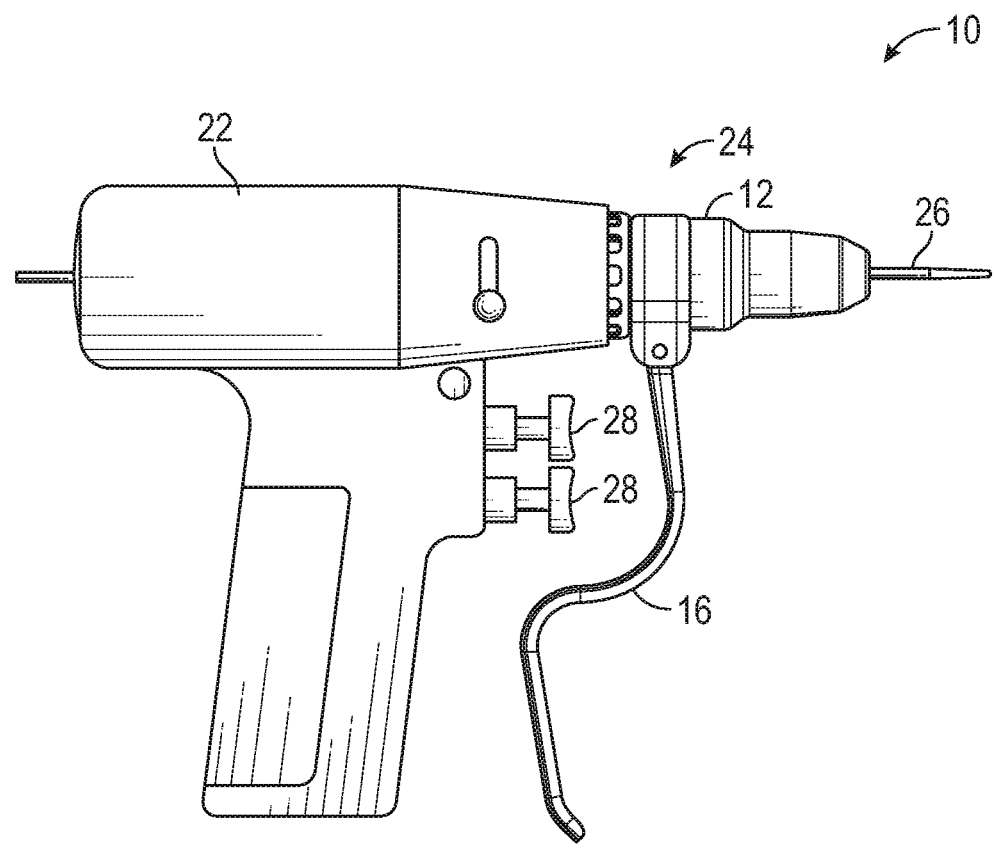
FIG. 2 is a schematic side view of an illustrative apparatus for driving wires according to an aspect of the disclosure.

The hand piece 22 of the pin wire driver 24 may include one or more triggers 28 (e.g., universal hand piece triggers, attachment specific hand piece triggers, or any other type of hand piece trigger), as shown in FIG. 2. For example, the hand piece 22 of the pin wire driver 24 may include one trigger 28, two triggers 28 (as shown in FIG. 2), three triggers 28, four triggers 28, or more triggers 28. In some instances, when there are two or more triggers 28, actuating a first one of the triggers 28 may cause rotation of a received pin or wire 26 in the clockwise direction and actuation of the other of the triggers 28 may cause rotation of the received pin or wire in the counter-clockwise direction. Alternatively, or in addition, the various triggers 28 may control the speed of rotation of a received pin or wire 26.

Figure 3A:
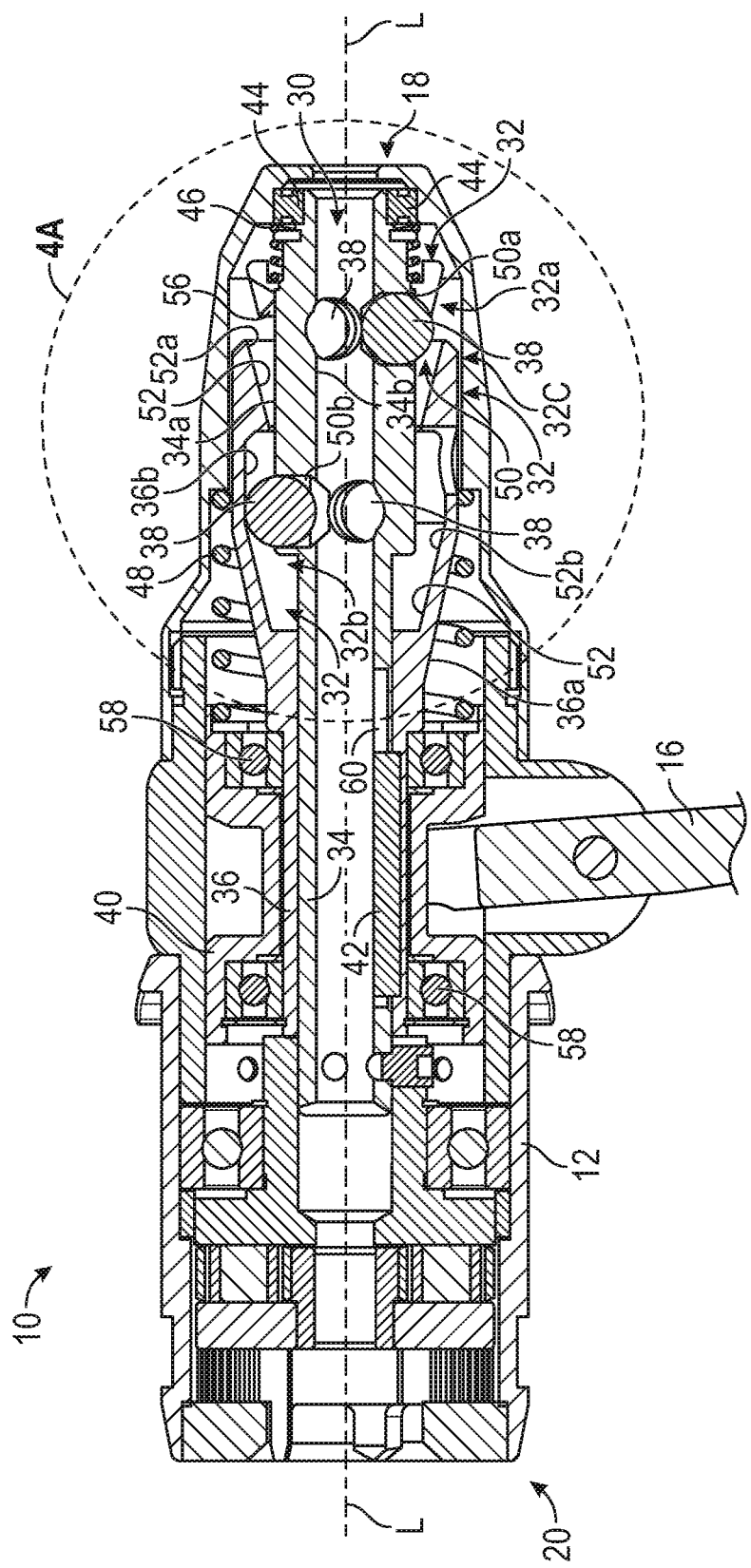
FIGS. 3A and 3B are schematic cross-sectional views of the attachment apparatus for driving wires depicted in FIG. 1, taken along line 3-3.
Figure 3B:
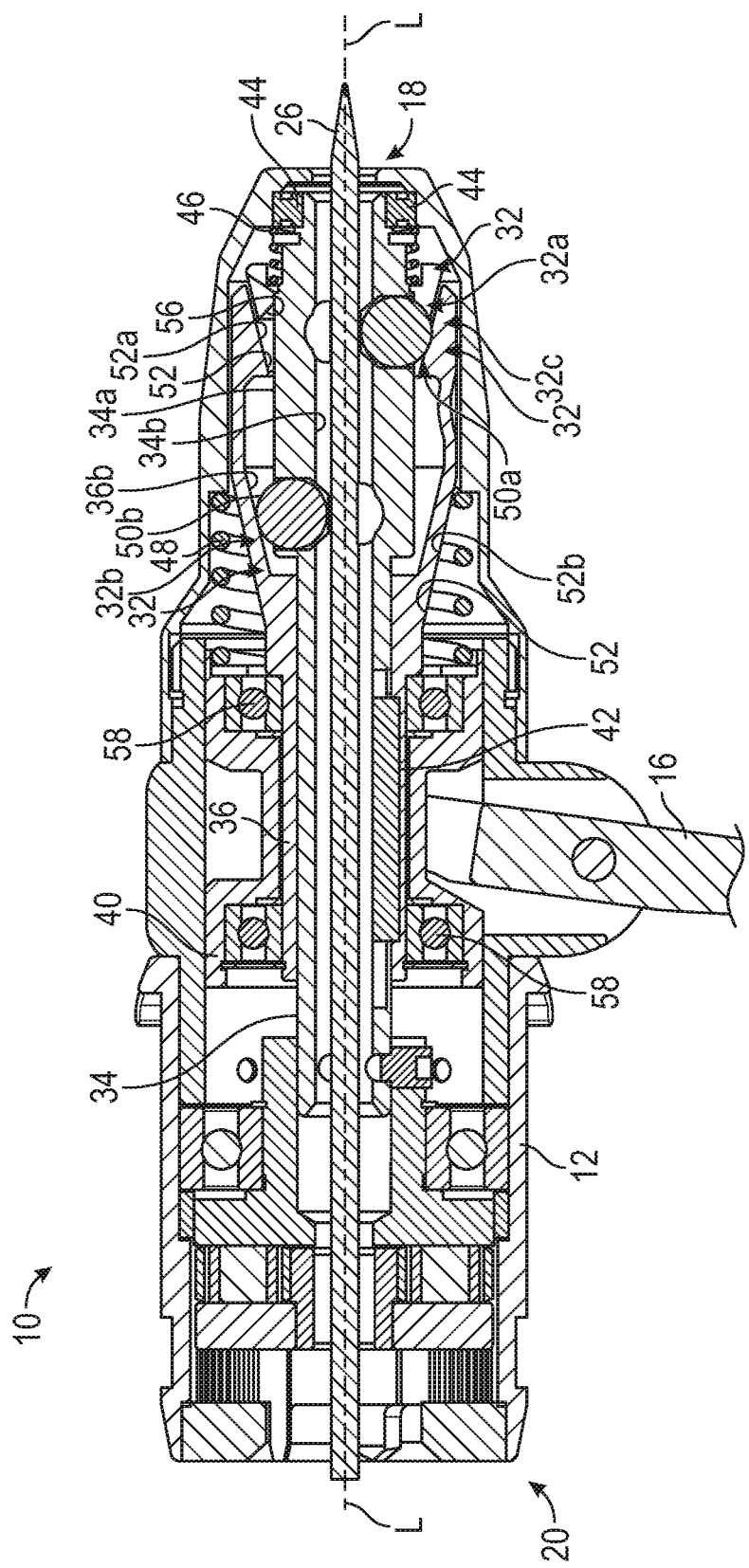

The body 12 of the pin wire driver attachment 10 may include gearing 20 configured to engage mating gears in a hand piece 22 of a pin wire driver 24. The gearing 20, as shown in FIGS. 3A and 3B, of the body 12 and/or the gearing of the hand piece 22 may be any type of gearing. In one example, the gearing 20 of the body 12 and the gearing of the hand piece 22 may be planetary gearing (e.g., two-stage planetary gearing or other planetary gearing) or any other type of gearing. Such gearing of the hand piece 22 may be caused to rotate in response to actuation of one or more of the triggers 28, which may in turn cause rotation of one or more features at least partially within the body 12 of the pin wire driver attachment 10.

The pin wire driver attachment 10 when connected to the hand piece 22 and/or when separated from the hand piece 22 may be capable of applying one or more similar or different forces to a pin or wire 26 received in a lumen 30 of thereof. In some illustrative instances, the pin wire driver attachment 10 may be capable of applying a force to a received or inserted pin or wire 26 at or adjacent each of one or more holding features 32.

In some cases, there may be more than two similar or dissimilar forces applied to the received or inserted pin or wire 26 at the two or more holding features 32 positioned along the lumen 30 of the pin wire driver attachment 10, where two or more of the two or more forces may be applied simultaneously with one another or at different times. For example, a first force may be applied to a received or inserted pin or wire 26 at a first holding feature 32a, a second force may be applied to the received or inserted pin or wire 26 at a second holding feature 32b, and/or a third force may be applied to the received or inserted pin or wire 26 at a third holding feature 32c, where one or more of the first, second, and/or third forces may be applied to the received pin or wire 26 simultaneously with one another or at different times. Although a first holding feature 32a, a second holding feature 32b, and a third holding feature 32c are labeled as such in FIGS. 3A and 3B, any holding feature 32 may be a first holding feature, a second holding feature, a third holding feature, and so on. The holding features 32 are further described below.

FIGS. 3A and 3B depict interior components or features of the pin wire driver attachment 10 taken along line 3-3 of FIG. 1 when the handle 16 is in a relaxed, neutral, spring biased, and/or natural position (FIG. 3A) and when the handle 16 is in an engaged and/or actuated position (FIG. 3B). The inner members or features of the pin wire driver attachment 10 may include, among other features, gearing 20, a first shaft 34, a second shaft 36, one or more engaging features 38 (e.g., ball bearings, other types of bearings, inserts, and/or other engaging features), plunger 40, a key 42, one or more stabilizing mechanisms 44 (e.g., bearings), and/or one or more other interior components or features. In some instances, the pin wire driver attachment 10 may be configured such that substantially all rotating parts of the pin wire driver attachment 10 are located within a body 12 thereof.

In some instances, the first shaft 34 may be a cannulated shaft with one or more at least partially rounded surfaces (e.g., at least partially rounded outer and/or inner surfaces). The lumen 30 may extend through the first shaft 34 and may be configured to receive the pin or wire 26 therethrough. The cannulated first shaft 34 may facilitate receiving any length pins or wires 26, as the open ends of the first shaft 34 will not limit a length of the received pin or wire 26.

Illustratively, the first shaft 34 may be at least partially positioned within the body 12 and may at least partially define the lumen 30 along longitudinal axis L-L. The first shaft 34 may be positioned substantially concentric about or around the longitudinal axis L-L and/or may be rotatable about the longitudinal axis L-L. In some cases, the first shaft 34 within the body 12 may be substantially stationary or stationary in the axial or longitudinal direction.

A distal end of the first shaft 34 may be positioned at or proximately proximal the opening 18 of the body 12. At or near the distal end of the first shaft 34, one or more stabilizing mechanisms 44 (e.g., one or more bearings) may provide a spacer between the body 12 and the outer surface 34a of the distal end of the first shaft 34. In one example, the stabilizing mechanism 44 may be a stabilizing bearing configured to support the first shaft 34 with respect to the body 12 and facilitate rotation of the first shaft 34 about the longitudinal axis L-L with respect to, relative to, or independent of the body 12.

In some instances, the first shaft 34 may include one or more openings 50 each for receiving an engaging feature 38 such as a spherical bearing or other engaging feature 38, where the one or more openings 50 may extend through the first shaft 34 from an outer surface 34a to an inner surface 34b of the first shaft 34. The one or more openings 50 for receiving engaging features 38 may be spaced (e.g., equally or unequally spaced) around the circumference of the first shaft 34 at one or more axially spaced locations. For example, as 25 shown in FIGS. 3A and 3B, a first set of openings 50a are shown at a first axial position along the first shaft 34 and a second set of openings 50b are shown at a second axial position along the first shaft 34, where the second axial position along the first shaft 34 may be axially spaced from the first axial position. In the example, the openings 50 of each set of openings 50a and 50b may be circumferentially spaced (e.g., equally spaced or spaced otherwise) about the first shaft 34 and/or may include one, two, three (as shown in FIGS. 3A-4C), four, or more openings 50. Further, in the example, each opening 50 may receive a single engaging feature 38 (e.g., a ball bearing or other insert).

Illustratively, the engaging features 38 may be any feature having any size, where the engaging feature is capable of extending at least partially through an opening 50 in a wall of the first shaft 34 and into the lumen 30 and is capable of releasably engaging a received pin or wire 26 extending at least partially through the lumen 30. For example, the engaging features 38 may be ball bearings or other inserts. The engaging features 38 may have a diameter less than 5.0 mm, less than 10 mm, less than 15 mm, less than 20 mm, between 1 mm and 20 mm, 5 mm and 15 mm, 5 and 10 mm, or less than any other diameter such as, for example, a diameter of 1.0 mm, 1.5 mm, 2.0 mm, 2.5 mm, 3.0 mm, 3.5 mm, 4.0 mm, 4.5 mm, 5.0 mm, 5.5 mm, 6.0 mm, and so on, as desired.

In some instances, the engaging features 38 received within the distal most set of openings 50 (e.g., the first set of openings 50*a*, as shown in Figures) may be biased and/or urged radially inward toward the longitudinal axis L-L in a passive manner with a biasing mechanism. In one example, the biasing mechanism may include a spring 46 and a ramped or an angled hold feature 54 (e.g., a ring member having an angled or ramped surface 56 or other hold feature) that may be positioned at least partially within the body 12 and/or about the first shaft 34, such that the spring 46 may bias or urge the angled hold feature(s) 54 in an axial direction toward a set of openings 50 (e.g., a distal most set of openings, such as the first set of openings 50*a*) having engaging features 38 positioned therein to engage one or more of those engaging features 38 against the ramped surface 56 of the holding feature 54 and automatically apply a retention force against a pin or wire 26 received within or inserted into the lumen 30 of the first shaft 34. The angled hold feature(s) 54 may be configured to passively or automatically abut or engage engaging features 38 such that engaging features 38 may be biased radially inward toward the longitudinal axis L-L to automatically or passively engage a pin or wire 26 received within the lumen 30 of the first shaft 34.

In one instance, an angled or ramped surface 56 of the angled hold feature 54 may be configured such that the angled or ramped surface 56 abuts the engaging feature 38 and urges the engaging feature 38 radially inward toward the longitudinal axis L-L of the first shaft 34. Illustratively, the angled or ramped surface 56 of the angled hold feature 54 may be so configured such that the angled or ramped surface 56 may be at 40 degrees, at 45 degrees, at 50 degrees, between 35 degrees and 55 degrees, between 40 degrees and 50 degrees, or at or between other oblique angles with respect to the longitudinal axis L-L to urge the engaging features toward the longitudinal axis L-L.

Figure 4A:
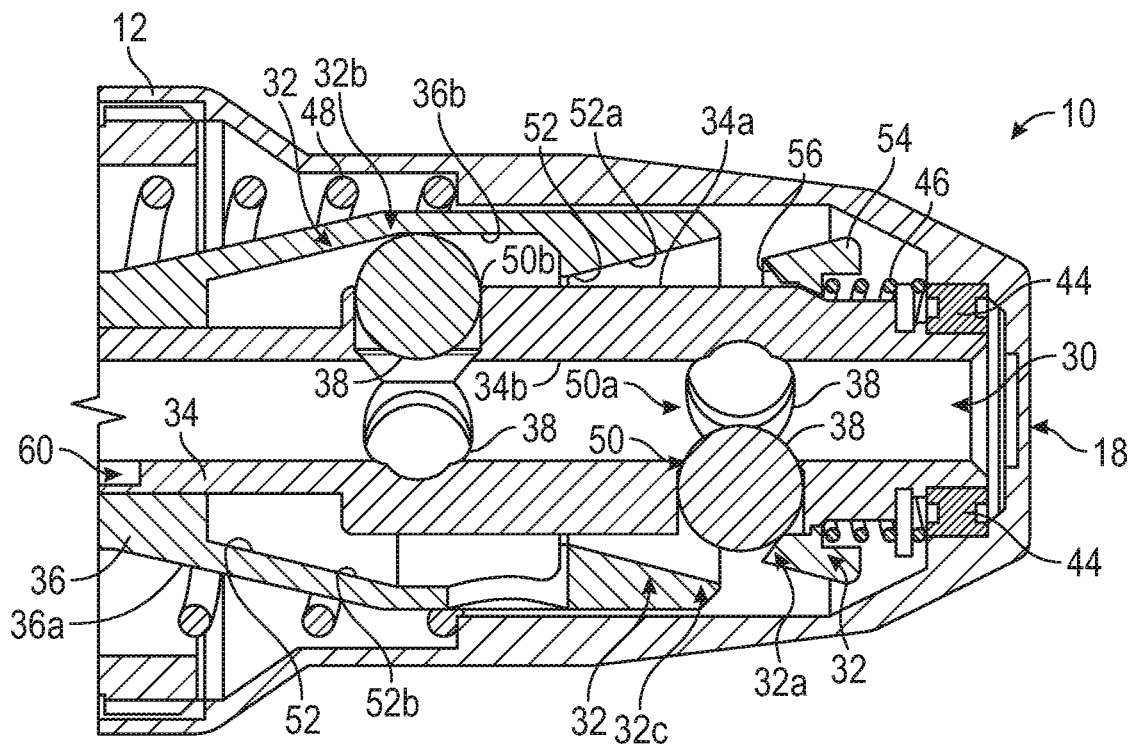
FIGS. 4A 4C are enlarged cross-sectional views of a portion of the attachment apparatus for driving wires depicted in FIG. 3A.
Figure 4B:
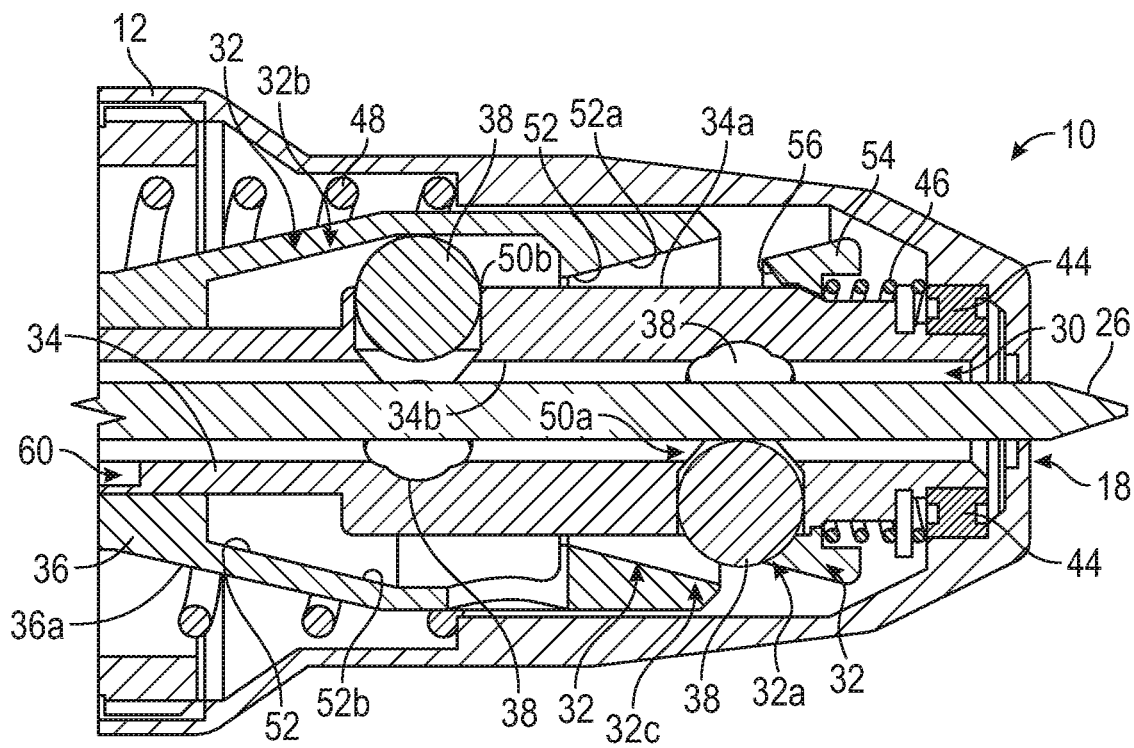

As the engaging features 38 of the distal most set of openings 50 may be biased toward the longitudinal axis L-L, these engaging features 38 may automatically and/or passively engage and/or hold a pin or wire 26 received within the lumen 30 of the first shaft therein. The received pin or wire 26 may urge engaging features 38 away from the longitudinal axis L-L and the first spring 46 may counteract the force applied to the engaging features 38 by the pin or wire 26 to hold the pin or wire 26 within the body 12 of the pin wire driver attachment 10, as shown in FIG. 4B. The first spring 46 may have a spring constant that allows for insertion of the pin or wire 26 within the lumen 30 of the first shaft 34, but is also configured to apply force through the engaging features 38 to the received pin or wire 26 to passively hold the pin or wire 26 within the body 12.

The second shaft 36 may have one or more rounded surfaces (e.g., one or more at least partially rounded exterior surface 36*a* and/or one or more at least partially rounded interior surface 36*b*) and may be at least partially positioned around the first shaft 34 and at least partially positioned within the body 12 of the pin wire driver attachment 10, as shown in FIGS. 3A and 3B. Illustratively, the second shaft 36 may be positioned concentrically or otherwise around the longitudinal axis L-L and/or the first shaft 34. In some instances, the second shaft 36 may be rotatable about the longitudinal axis and/or may be axially movable and/or adjustable (e.g., axially movable and/or adjustable in the direction of arrows 1-1). A key 42 may be positioned between the first shaft 34 and the second shaft 36 in opening 60 such that the first shaft 34 rotates with the second shaft 36. Thus, the first shaft 34 may rotate as the second shaft 36 rotates and vice versa, while the second shaft is capable of axial or longitudinal movement independent of the first shaft 34.

In one example, the handle 16 may be in operative communication with the second shaft 36 such that actuation of the handle 16 and/or release of the handle 16 may result in axial movement of the second shaft 36 along the longitudinal axis L-L relative to the first shaft 34 and the body 12. The key 42, configured to create a rotating connection between the first shaft 34 and the second shaft 36, may be positioned and/or configured such that the second shaft 36 may rotate with the first shaft 34, but may be movable in the axial direction independent of the first shaft 34. For example, the key 42 may engage the second shaft 36 and may slidingly fit within an opening 60 of the first shaft 34, such that the second shaft 36 may move axially independent of movement of the first shaft 34 and may rotate with the first shaft 34.

In some instances, the second shaft 36 may have one or more angled or ramped surfaces 52. For example, the second shaft 36 have a first ramped surface 52*a* and a second ramped surface 52*b*, where the second ramped surface 52*b* may be axially spaced from the first ramped surface 52*a*. Although the second ramped surface 52*b* is depicted in FIGS. 3A and 3B as being located proximal the first ramped surface 52*a*, either ramped surface 52 may be labeled first or second ramped surface 52*a*, 52*b*. The first ramped surface 52*a* and/or the second ramped surface 52*b* may extend at least partially around the interior surface 36*b* at one or more spaced locations, or the first ramped surface 52*a* and/or the second ramped surface 52*b* may extend entirely around the interior surface 36*b* of the second shaft 36.

The interior surface 36*b* of the first ramped surface 52*a* and/or the interior surface 36*b* of the second ramped surface 52*b* may be configured to engage the one or more engaging features 38. In one example, the first and/or second ramped surfaces 52*a*, 52*b* may engage one or more of the engaging features 38 when the handle 16 is actuated causing the second shaft 36 to move axially in a distal direction and/or at one or more other times.

The first ramped surface 52*a* may be configured to engage a first set of engaging features 38 at a desired time with respect to when the second ramped surface 52*b* engages a second set of engaging features 38 as the handle 16 is actuated to cause the second shaft 36 to move axially and engage the engaging features 38. In one example, the first ramped surface 52*a* may engage a first set of engaging features 38 simultaneously with when the second ramped surface 52*b* engages a second set of engaging features 38 proximal the first set of engaging features 38 as the handle 16 is actuated. In another example, the first ramped surface 52*a* may engage a first set of engaging features 38 after the second ramped surface engages a second set of engaging features 38 proximal the first set of engaging features as the handle 16 is actuated.

When the interior surfaces 36*b* of the ramped surfaces 52 engage an engaging feature 38, the engaging feature 38 may be urged radially inward within the openings 50 of the first shaft 34 toward the longitudinal axis L-L about which the first shaft 34 is positioned. When a pin or wire 26 is positioned within the lumen 30 of the first shaft 34, the engaging features 38 may actively engage the pin or wire 26, as shown for example in FIGS. 3B and 4C, as the second shaft 36 is actuated distally.

The ramped surfaces 52 may be configured at any desired oblique angle with respect to the longitudinal axis L-L. Illustratively, the ramped surface 52 may be arranged at an angle of 40 degrees, of 45 degrees, of 50 degrees, between 35 degrees and 55 degrees, between 40 degrees and 50 degrees, or at or between other oblique angles with respect to the longitudinal axis L-L to urge the engaging features toward the longitudinal axis L-L.

In some instances, the handle 16 may engage or interact with a plunger 40 that may be positioned about and/or in communication with the second shaft 36. When the handle 16 is actuated, the plunger 40 may be engaged and moved axially to actuate movement of the second shaft 36 in the axial direction.

In some cases, one or more bearings 58 may be positioned between the second shaft 36 and the plunger 40. The bearings 58 may facilitate rotational movement of the second shaft 36 independent of the plunger 40. Illustratively, one, two, or more bearings 58 may be utilized to facilitate rotational movement between the second shaft 36 and the plunger 40, while allowing for axial movement of the second shaft 36 with axial movement of the plunger 40.

The plunger 40 and the second shaft 36 may be biased proximally in the axial direction by the second spring 48 to bias the angled or ramped surfaces 52 of the second shaft 36 away from engagement with one or more engagement features 38. In one example, the second spring 48 may extend between the body 12 or other feature in communication with the body 12 and the one or more features of the plunger 40 (as shown in FIGS. 3A and 3B) and the second shaft 36. When the handle 16 is actuated, the actuated handle 16 may interact with the plunger 40 to move the plunger 40 and/or the second shaft 36 axially in a distal direction against the bias of the second spring 48 to cause active engagement of the engaging features 38 with a received pin or wire 26. Alternatively, and in some instances, the second shaft 36, the plunger 40, the second spring 48, and/or the handle 16 may be configured such that the second shaft 36 may be biased in the distal direction and actuation of the handle 16 may cause proximal movement of the second shaft 36 with respect to the first shaft 34 and/or the body 12 to actively apply or to apply an active force to a pin or wire 26 received within the lumen 30 of the first shaft 34.

Figure 4C:
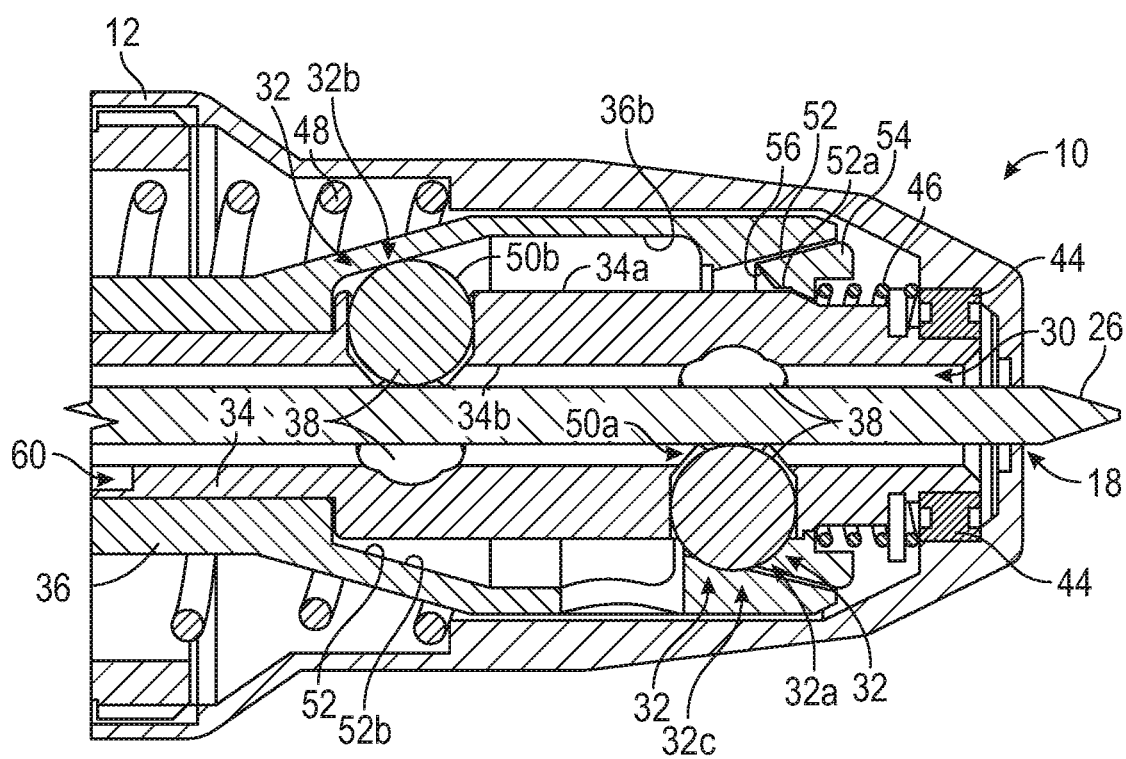
Figure 5:
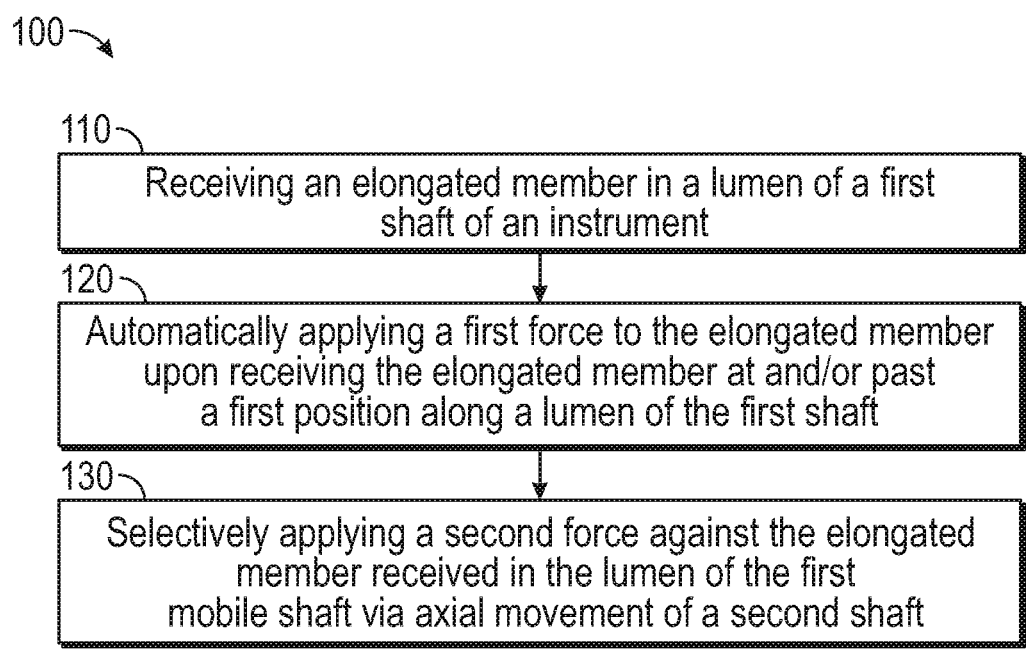
FIG. 5 is a schematic flow diagram of a method of using an illustrative attachment apparatus for driving wires according to an aspect of the disclosure.

The second spring 48 may have a spring constant that biases the plunger 40 and second shaft 36 axially in a proximal direction, where actuation of the handle 16 may overcome a force acting on the plunger 40 and/or the second shaft 36 to move the second shaft 36 in a proximal direction such that the second shaft 36 engages the engaging features 38 to apply an active force to a received pin or wire 26, as shown in FIG. 4C. The spring constant of the second spring 48 may operate to move the plunger 40 and/or the second shaft 36 axially in a proximal direction when the handle 16 is released to remove an active force being applied to the pin or wire 26 when the handle 16 is actuated. In some instances, the active force applied to a received pin or wire 26 during the actuation of the handle 16 may be greater than the passive force applied to the received pin or wire 26, where the passive force is substantially constantly applied to the received pin or wire 26 except when the active force is applied at the engaging features 38 in the set of openings 50 at which the passive force is applied to the received pin or wire 26.

In one or more alternative instances, the active force may be applied to a received pin or wire 26 in one or more manners that differ from the application of the active force described above. For example, the second shaft 36, the second spring 48, the engaging features 38, and/or other features may be configured to apply an active force to a received pin or wire 26 when in a natural, neutral, or relaxed position, and the handle 16 may be actuated to selectively remove the active force from the received pin or wire 26.

As discussed above, the pin wire driver attachment 10 may include holding features 32 to apply one or more passive and/or active forces to a pin or wire 26 received in the pin wire driver attachment 10. Holding features 32 as discussed herein may include one or more features utilized to either actively or passively engage a pin or wire 26 that is received within the lumen 30 of the first shaft 34. In some instances, the pin wire driver attachment 10 may include one or more holding features 32 that may apply a passive force to a received pin or wire 26 and one or more holding features 32 that may apply an active force to a received pin or wire 26. There may be any number of holding features 32, for example, there may be one holding feature, two holding features, three holding features, four holding features, or more holding features, if desired.

In one example, the pin wire driver attachment 10 may include two holding features 32. In such an instance a first holding feature 32a may be located a first position along the longitudinal axis L-L and/or may include a distal most set of engaging features 38 (e.g., one or more engaging features 38), an angled hold feature 54, a spring 46, and/or other features to constantly and/or passively (e.g., without actuation or releasing of a trigger, handle, or other mechanism) apply a force (e.g., a first force) to a pin or wire 26 received within the lumen 30 and extending to and/or beyond the first position along the longitudinal axis L-L. A second holding feature 32b may be located at a second position along the longitudinal axis L-L spaced proximally from the first position and/or at the first position along the longitudinal axis L-L. The second holding feature 32b may include a set of engaging features 38 (e.g., one or more engaging features 38) that are spaced proximally from the set of engaging features 38 of the first holding feature 32a or the engaging features 38 of the first holding feature 32, the second spring 48, and/or a ramped surface 52 of the second shaft 36 that may engage the set of engaging features 38 at the second position or first position along the longitudinal axis L-L to apply an active force or to actively apply a force (e.g., a second force) to the received pin or wire 26 at the second position or first position along the longitudinal axis L-L in response to actuating the handle 16.

As shown in FIGS. 3A-4C, the pin wire driver attachment 10 may include three holding features 32, where one holding feature may apply a passive force to a received pin or wire 26 and two holding features may apply an active force to the received pin or wire 26. Illustratively, a first holding feature 32a may be located at a first position along the longitudinal axis L-L and/or may include a distal most set of engaging features 38, an angled hold feature 54, a first spring 46, and/or other features to constantly and/or passively (e.g., without actuation of a trigger, handle, or other mechanism) apply a force (e.g., a first force) to a pin or wire 26 received within the lumen 30 and extending to and/or beyond the first position along the longitudinal axis L-L. A second holding feature 32b may be located at a second position along the longitudinal axis L-L and/or may include a set of engaging features 38 that are spaced proximally from the set of engaging features 38 of the first holding feature 32a, the second spring 48, and/or a ramped surface 52 (e.g., a second ramped surface 52*b*) of the second shaft 36 that may engage the set of engaging features 38 at the second position along the longitudinal axis L-L to apply an active force or to actively apply a force (e.g., a second force) to the received pin or wire 26 at the second position along the longitudinal axis L-L in response to actuating the handle 16. In some optional instances, a third holding feature 32*c* may be located at the first position along the longitudinal axis L-L and/or may include the set of engaging features 38 that are located at the first position along the longitudinal axis L-L, the second spring 48, and/or a ramped surface 52 (e.g., a first ramped surface 52*a*) of the second shaft 36 that may engage the set of engaging features 38 at the first position along the longitudinal axis L-L to apply an active force or to actively apply a force (e.g., a third force which many be equal to or different than the second force) to the received pin or wire 26 at the first position along the longitudinal axis L-L in response to actuating the handle 16.

In some instances, the first force, the second force, and the third force applied to a received pin or wire 26 may equal the same amount of force. Alternatively, one or more of the first force, the second force, and the third force may be different from at least one other of the first force, the second force, and the third force. In the example described above, the amount of force of the first force applied to the received pin or wire 26 may be less than the amount of force of each of the second force and the third force. In some instances, the amounts of the second force and the third force may be equal or may be different.

Any one of the holding features 32 may be numbered differently, for example, any holding feature 32 may be a first holding feature and any next holding feature 32 may be a second holding feature and any next holding feature 32 may be a third holding feature. The numbering of the holding features 32 and the numbering of any features herein described is done to distinguish between features and is not meant to be limiting in any way other than to indicate there is at least that many of those numbered features.

In some instances, a pin wire driver attachment 10 may be used in one or more methods. For example, the pin wire driver attachment 10 may be utilized in a method 100 of maintaining an elongated member in the pin wire driver attachment 10. The method 100 may include receiving a pin or wire 26 (e.g., an elongated member) in a lumen 30 of a rotatable first shaft 34 of the pin wire driver attachment 10. Upon receiving the pin or wire 26 at and/or past a first position along a longitudinal axis L-L of the lumen 30 of the first shaft 34, a first force may be automatically applied against the pin or wire 26 received in the lumen 30. A second force may be selectively applied against the pin or wire 26 received in the lumen 30 of the first shaft 34 of the pin wire driver attachment 10. In some instances, the second force may be selectively applied against the received pin or wire 26 via axial movement of a rotatable second shaft 36 of the pin wire driver attachment.

In some instances, the method 100 may include selectively applying a third force against the pin or wire 26 received in the lumen 30 of the first shaft 34 with the axial movement of the second shaft 36 that may or may not be used to apply the second force to the pin or wire 26. The first force and/or the second force may be applied to the pin or wire at the first position along the longitudinal axis L-L. The third force may be applied to the pin or wire 26 at a second position along the longitudinal axis L-L. Illustratively, the second position along the longitudinal L-L axis may be spaced a distance proximal from the first position along the longitudinal axis of the first shaft 34. In some cases, the first position may be distal the second position so as to apply a passive force or automatic force to a received pin or wire 26 upon receiving only a portion of the pin or wire 26. Alternatively, or in addition, to the relative locations of the first and second positions discussed herein, the first and second positions, or other positions, may be located at any position relative to one another along the longitudinal axis L-L, as desired.

The second force and/or the third force may be applied to a received pin or wire 26 through actuation of the handle 16. When the handle 16 is in its natural or neutral position (e.g., when the handle is not actuated or no force acting from exterior the body 12 is applied to the handle 16), the plunger 40 and the second shaft 36 may be biased in the proximal direction by the second spring 48 or other spring mechanism and there is no active force acting on any of the engaging features 38 by the second shaft 36. When the handle 16 is actuated (e.g., when the handle is squeezed and/or a force is applied to the handle 16), the plunger 40 may be forced distally by the handle 16 against a biasing force of the second spring 48. When the plunger 40 is forced distally, the plunger 40 may cause the second shaft 36 to move distally toward the distal end of the pin wire driver attachment 10 to engage the engaging features 38. The more force that is applied to the handle 16 to actuate the handle, the greater the active force is that is applied to the received pin or wire 26 via the engagement of the engaging features 38 by the angled or ramped surfaces 52 of the second shaft 36.

As the second shaft 36 moves distally, the angled or ramped surfaces 52 of the second shaft 36 may engage one or more of the engaging features 38 applying an inward and/or compression force onto the received pin or wire 26 through the engaging features. In some cases, the interaction between the engaging features 38 and the angled or ramped surfaces 52 may be such that each engaging feature 38 of each set of engaging features 38 (e.g., each set may include three engaging features 38 equally spaced circumferentially around the first shaft 34 and each set may be positioned at different positions along the longitudinal axis L-L) applies the same amount of force to the received pin or wire 26 as the other engaging features 38 of its set. After the handle 16 has been actuated and a suitable active force has been applied to the received pin or wire 26, the triggers 28 of a hand piece 22 in communication with the pin wire driver attachment 10 may be actuated to rotate the pin or wire 26 that is securely held within the pin wire driver attachment 10.

Although certain steps of the method of operation may be discussed herein in one or more particular orders, it is contemplated one or more methods of operation may follow these steps in other orders (including a plurality of steps being performed simultaneously), may include one or more further steps, or may include further steps in any order.

Figure 6A:
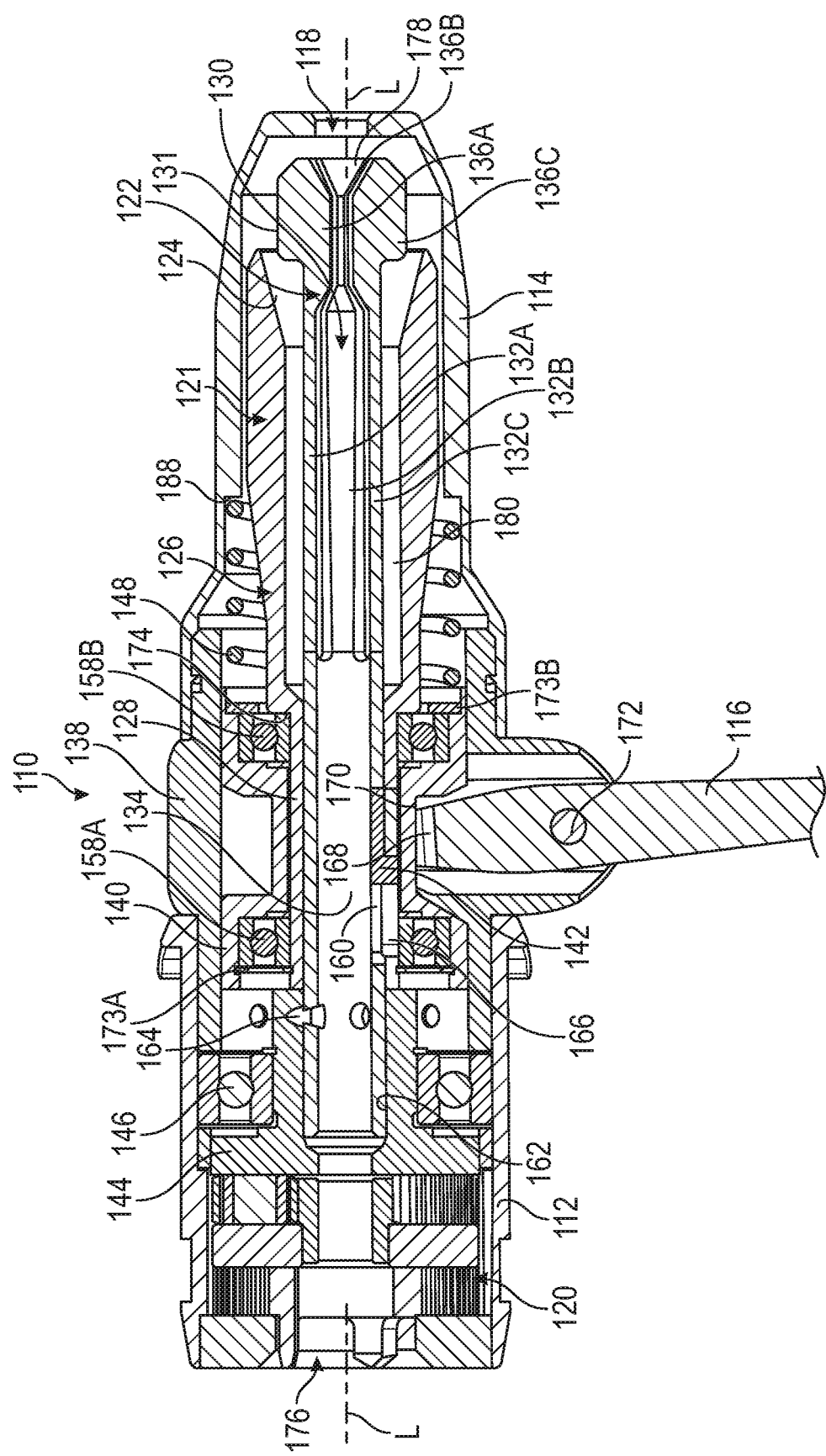
FIG. 6A is a schematic cross-sectional view of another embodiment of an attachment apparatus for use with the apparatus for driving wires shown in FIG. 2, the attachment apparatus having a mobile shaft with an angled contact surface and a flexible collet with flat contact surfaces.

FIG. 6A is a schematic cross-sectional view of an embodiment of attachment apparatus 110 for use with an apparatus for driving wires, such as hand piece 22 shown in FIG. 2. Attachment apparatus 110 can comprise body 112, nose 114, and handle 116. Opening 118 can be located in nose 114 and can provide access to lumen 130 extending through attachment apparatus 110. Lumen 130 and attachment apparatus 110 can extend along longitudinal axis L-L. Body 112 can include gearing 120 that can be part of a drive input to rotate pin wires disposed in lumen 130. Elements 110-120 are configured similarly and operate similarly to elements 10-20 descried previously with reference to FIGS. 1-4C. Likewise, as discussed below, plunger 140, spring 148, bearings 158 and opening 160 are similar to plunger 40, spring 48, bearings 58 and opening 60.

Attachment apparatus 110 can also comprise mobile shaft 121 and flexible collet 122. Mobile shaft 121 can comprise contact surface 124, driver portion 126 and shaft portion 128. Flexible collet 122 can include shoulder 131, flexible arms 132A-132D (only arms 132A-132C are visible in FIGS. 6A and 6B) and shaft portion 134. Shoulder 131 can include tabs 136A 136D (only tabs 136A-136C are visible in FIGS. 6A and 6B).

Body 112 can be connected to nose 114 via handle housing 138 to form a hollow assembly through which lumen 130 can extend. Plunger 140 can be located in handle housing 138 to receive shaft portion 128 of mobile shaft 121 and shaft portion 134 of flexible collet 122. Shaft portion 128 and shaft portion 134 can be coupled via key 142. Gearing 120 can be located in body 112 and can be configured to receive an input, such as a rotational drive shaft from hand piece 22 (FIG. 2). Gearing 120 can also be configured to provide output to hub 144 via any suitable means. Hub 144 can be held in body 112 via bearings 146. Shaft portion 128 and shaft portion 134 can be held in plunger 140 via bearings 158A and 158B. Spring 148 can be positioned between nose 114 and plunger 140.

Shaft portion 134 of flexible collet 122 can be inserted into socket 162 within hub 144. Hub 144 can be rotated via interaction with gearing 120. Shaft portion 134 can be coupled to hub 144, such as via a pin at bore 164, so that shaft portion 134 can rotate with hub 144. Shaft portion 128 of mobile shaft 121 can be concentrically positioned over shaft portion 134. Shaft portion 128 can include opening 166 and shaft portion 134 can include opening 160. Openings 166 and 160 can comprise elongate slots that can align to receive key 142. Openings 166 and 160 can be sized to have the approximately the same circumferential width as key 142 so that shaft portion 128 and shaft portion 134 rotate together. Opening 166 can be longer than the axial length of key 142 so that mobile shaft 121 can be axially translated along shaft portion 134 of flexible collet 122. Opening 160 can be longer than the axial length of key 142 to facilitate assembly of key 142 to shaft portions 128 and 134.

Shaft portions 128 and 134 can be inserted into bearings 158A and 158B within plunger 140. Lock rings 173A and 173B can be positioned against bearings 158A and 158B, respectively, to assist in retaining bearings 158A and 158B within plunger 140. Thus, shaft portions 128 and 134 can rotate within plunger 140 under rotational input from hub 144. Mobile shaft 121 can be translated against shaft portion 134 via movement of plunger 140 under input from handle 116. Handle 116 includes end 168 that can engage channel 170 in plunger 140. As a bottom (with respect to the orientation and configuration of FIG. 6A) portion of handle 116 is pulled proximally, end 168 can rotate distally forward at pin 172 to push plunger 140 and bearings 158A and 158B along shaft portion 134. Bearings 158B can be pushed against shoulder 174 of mobile shaft 121 to push mobile shaft 121 distally. Shoulder 174 can be located at the juncture of shaft portion 128 and driver portion 126.

Figure 6B:
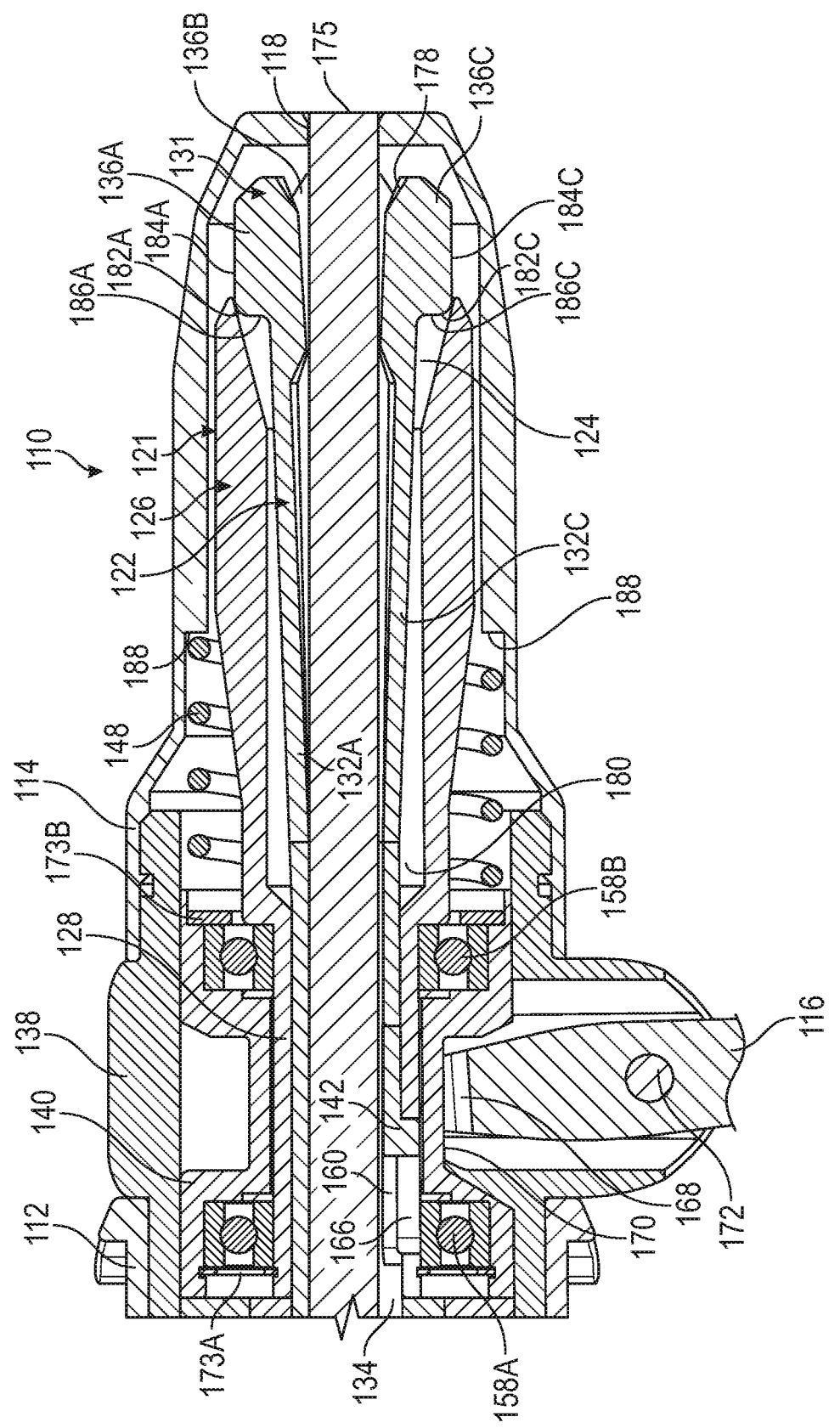
FIG. 6B is a schematic cross-sectional view of the attachment apparatus of FIG. 6A with a pin inserted into the flexible collet.

FIG. 6B is a schematic cross-sectional view of attachment apparatus 110 of FIG. 6A with pin wire 175 inserted into flexible collet 122. Pin wire 175, or a pin or wire, such as pin or wire 26 described above, can be inserted into lumen 130 such as at opening 176 (FIG. 6A) for advancement toward opening 118 via attachment apparatus 110. Pin wire 175 can penetrate through tip passage 178 in shoulder 131 and out opening 118 for insertion into a medium, such as bone of a patient. Tip passage 178 can be formed between tabs 136A-136D extending from flexible arms 132A-132D, respectively. Thus, as pin wire 175 is inserted into shoulder 131 from within lumen 130, flexible arms 132A-132D can flex to permit pin wire 175 into tip passage 178. Flexible arms 132A-132D can flex over a range of deflections to accommodate pin wires of different sizes, e.g., different diameters. Driver portion 126 of mobile shaft 121 can have a larger outer diameter than shaft portion 128 so that internal passageway 180 extending through mobile shaft 121 can have a larger diameter within driver portion 126 than shaft portion 128 to, for example, permit flexible arms 132A-132D to deflect outward. Outward deflection of flexible arms 132A-132D via pin wire 175 can cause flexible arms 132A 132D to apply pressure to pin wire 175 to retain pin wire 175 within lumen 130. As such, pin wire 175 may not be removed from lumen 130 under its own weight. However, in order to retain pin wire 175 within lumen 130 so that pin wire 175 can be advanced and driven into a medium, such as bone, attachment apparatus 110 can be actuated by handle 116 to more firmly grasp pin wire 175.

Mobile shaft 121 can be advanced distally to push driver portion 126 into contact with shoulder 131 of flexible collet 122. In particular, contact surface 124 can be pushed to engage edges 182A 182D (only edges 182A 182C are visible in FIGS. 6A and 6B) of tabs 136A 136D. After initial contact, additional advancement of mobile shaft 121 can cause tabs 136A 136D to tend to deflect radially inward due to the angled nature of contact surface 124. In examples, contact surface 124 can have frusto-conical shape that increases in diameter in the proximal-to-distal direction. As such, the further mobile shaft 121 is advanced, the smaller the diameter of passageway 180 (at contact surface 124) becomes that is engaged with edges 182A 182D. Tabs 136A 136D and contact surface 124, therefore, form an engagement mechanism that allows flexible arms 132A-132D to push down on pin wire 175 with sufficient force to immobilize pin wire 175 when subject to axial loading, such as from a surgeon pushing pin wire 175 into bone. Angling or ramping of contact surface 124 can permit a variable amount of force from driver portion 126 to be applied to pin wires of different sizes depending on the degree to which handle 116 is moved. Shoulder 131 can be shaped to beneficially transfer force from contact surface 124 to pin wire 175. In the example shown in FIGS. 6A and 6B, tabs 136A 136D have a rectilinear shape with outer surfaces 184A 184D (only outer surfaces 184A 184C are visible in FIGS. 6A and 6B) and side surfaces 186A 186D (only side surfaces 184A 184C are visible in FIGS. 6A and 6B) forming edges 182C 182D. Edges 182A 182D can have a radius to distribute forces at the engagement with contact surface 124.

Figure 7A:
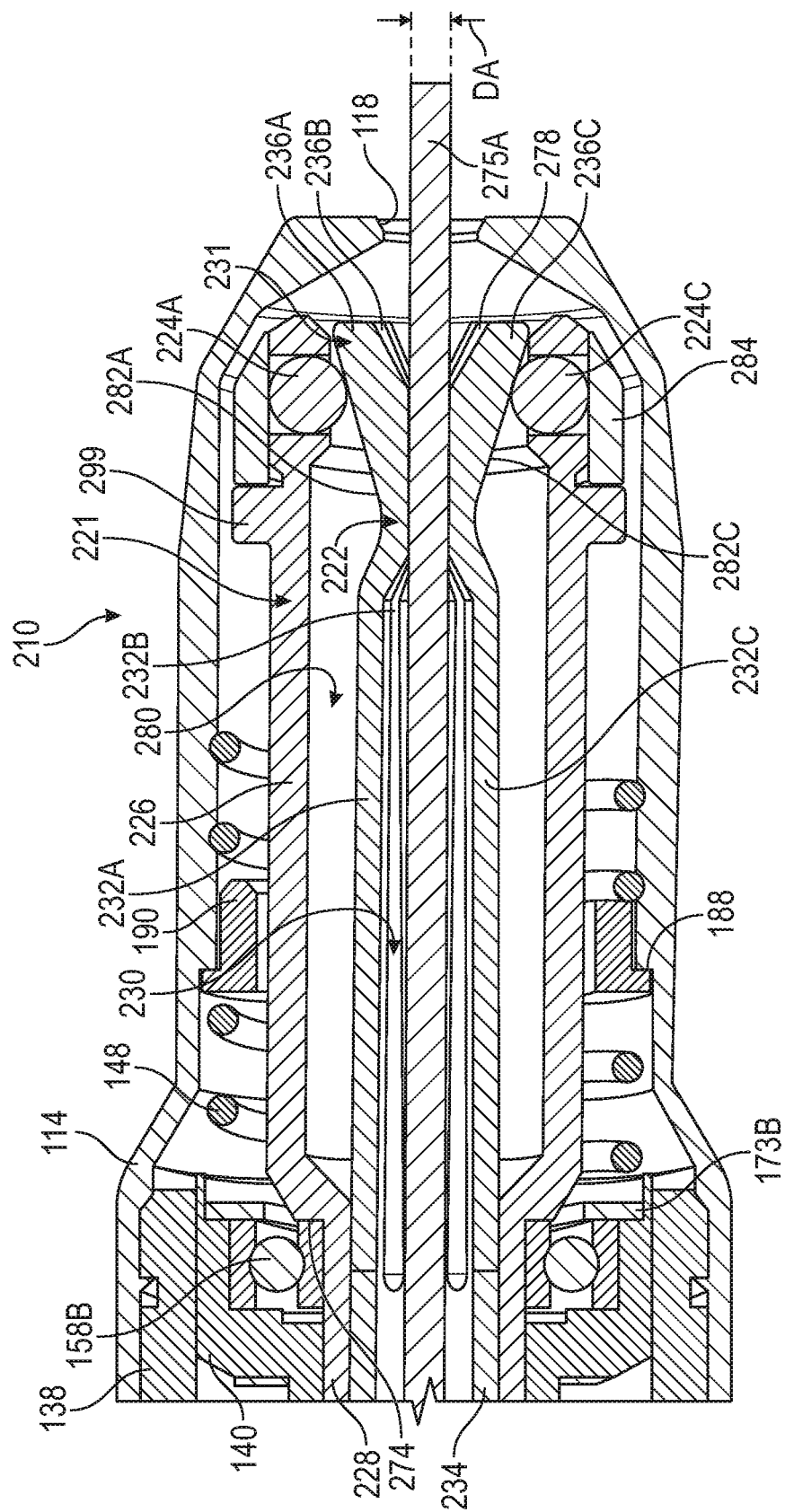
FIG. 7A is a schematic cross-sectional view of another embodiment of an attachment apparatus for use with the apparatus for driving wires shown in FIG. 2, the attachment apparatus having a mobile shaft with bearings and a flexible collet with angled contact surfaces engaging a small-sized pin.
Figure 7B:
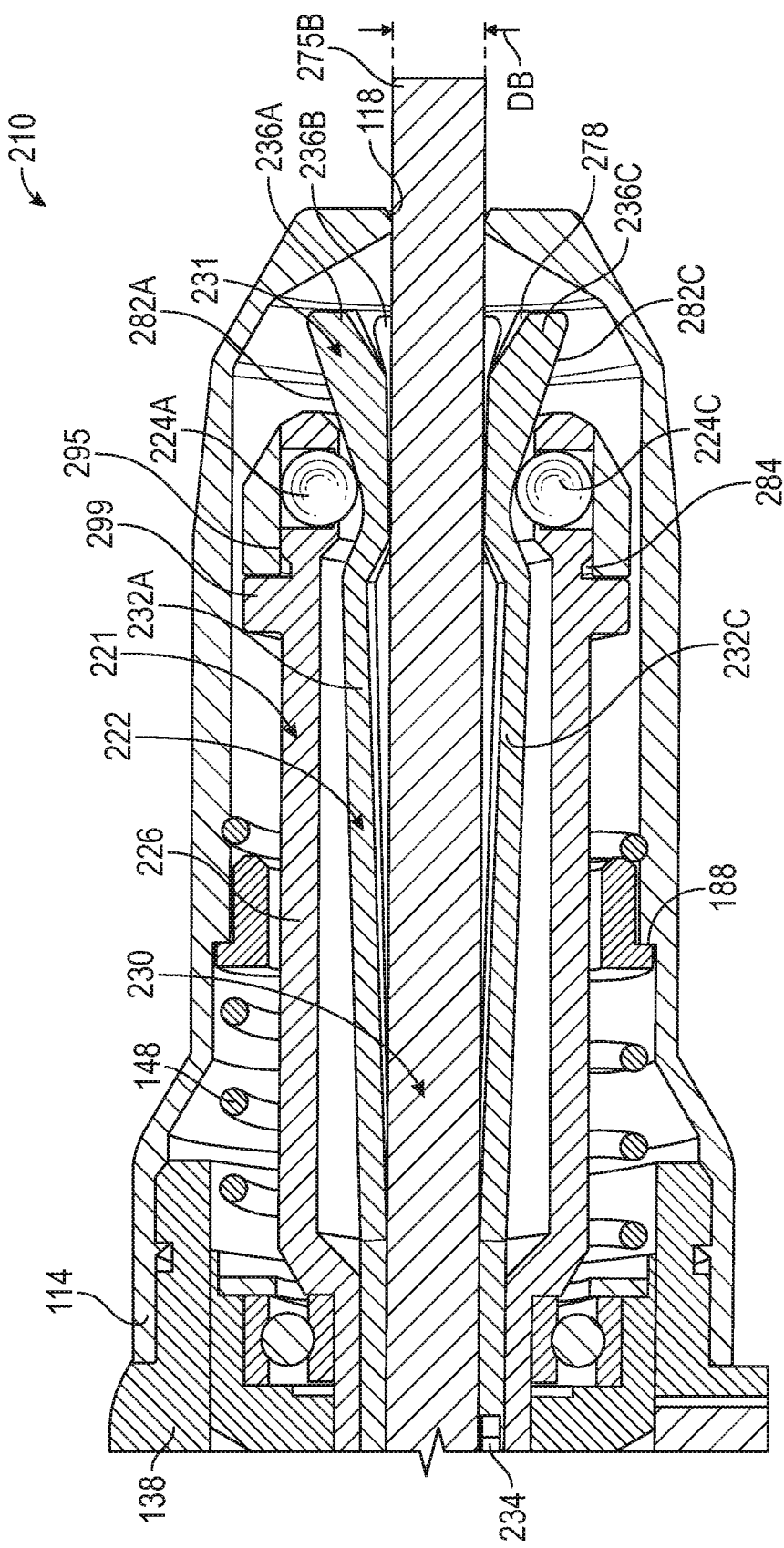
FIG. 7B is a schematic cross-sectional view of the attachment apparatus of FIG. 7A with a large-sized pin inserted into the flexible collet.

Distal advancement of plunger 140 from handle 116 can compress spring 148. Ends of spring 148 can be positioned to engage plunger 140, such as at bearings 158B, and nose 114, such as at shoulder 188. In the embodiment of FIGS. 7A and 7B, pin wire driver 210 can include collar 190 that engages shoulder 188. Collar 190 can provide a surface for spring 148 to push against and can prevent spring 148 from becoming caught between nose 114 and mobile shaft 221. Collar 190 can also act as a bearing to guide mobile shaft 221 through nose 114. Spring 148 can bias plunger 140 to a retracted state where contact surface 124 is disengaged from edges 182A 182D so that pin wire 175 is only being held by the force of flexible arms 132A-132D. Additionally, the bottom of handle 116 can be pushed forward so that end 168 can push plunger 140 proximally toward hub 144 and pull contact surface 124 away from shoulder 131.

In other examples, various engagement mechanisms can include contoured surfaces or other features and components to facilitate disengagement of driver portion 126 from flexible collet 122. In other examples of engagement mechanisms, edges 182A 182D can be replaced with chamfers between surfaces 184A 184D and surfaces 186A 186D, respectively, to increase the contact surface area with contact surface 124. Increasing the contact surface area between contact surface 124 and shoulder 131 can reduce the likelihood of contact surface 124 becoming stuck to or bound to shoulder 131, such as from galling. In other examples, the geometry of contact surface 124 and shoulder 131 can be reversed, such that shoulder 131 forms a frusto-conical surface and contact surface forms a point contact or segment contact area for the frusto-conical surface. In yet other examples, contact surface 124 can include bearings to facilitate engagement and disengagement between driver portion 126 and flexible collet 122, as shown in FIGS. 7A and 7B.

FIG. 7A is a schematic cross-sectional view of an embodiment of attachment apparatus 210 for use with an apparatus for driving wires, such as hand piece 22 shown in FIG. 2. Attachment apparatus 210 can comprise mobile shaft 221 and flexible collet 222. Mobile shaft 221 can comprise bearings 224A-224D (only bearings 224A and 224C are visible in FIG. 7A), driver portion 226 and shaft portion 228. Flexible collet 222 can include shoulder 231, flexible arms 232A 232D (only flexible arms 232A 232C are visible in FIG. 7A) and shaft portion 234. Shoulder 231 can include tabs 236A-236D (only tabs 236A 236C are visible in FIG. 7A). FIG. 7A is shown with flexible collet 222 having contained therein pin wire 275A having diameter $D_A$.

FIG. 7B is a schematic cross-sectional view of attachment apparatus 210 of FIG. 7A with flexible collet 222 having contained therein pin wire 275B having diameter $D_B$. Pin wire 275B is larger than pin wire 275A such that diameter $D_B$ is larger than diameter $D_A$ and flexible arms 232A-232D in FIG. 7B are flexed. Other than pin wires 275A and 275B, FIGS. 7A and 7B include the same reference numbers and are discussed concurrently to explain the operation of mobile shaft 221 and flexible collet 222. Plunger 140 operates in the same manner as discussed with reference to FIGS. 6A and 6B to push mobile shaft 221 distally to engage flexible collet 222 and immobilize pin wires 275A and 275B.

Shaft portions 228 and 234 can include openings 266 and 260 (FIGS. 8 and 9), respectively, similar to openings 166 and 160 (FIG. 6A), so shaft portions 228 and 234 can be linked together using key 142 (FIG. 6A). Shaft portions 228 and 234 can be inserted into hub 140 to rotate mobile shaft 221 and flexible collet 222. Shaft portion 234 can also include bore 264 (FIG. 9), similar to bore 164 (FIG. 6A), to link flexible collet 222 with hub 140. Hub 140 can be advanced to push mobile shaft 221 along shaft portion 234 of flexible collet 222 via engagement of bearings 158B with shoulder 274. Application of force to handle 116 (FIG. 6A) can cause hub 140 and mobile shaft 221 to move along shaft portion 234 and overcome force from spring 148. Driver portion 226 can thereby engage shoulder 231 to deflect flexible arms 232A-232D radially inward, as discussed in greater detail below.

Pin wire 275A or 275B can be inserted into lumen 230 such as at opening 176 (FIG. 6A) for advancement toward opening 118 via attachment apparatus 210. Pin wire 275A or 275B can penetrate through tip 278 in shoulder 231 and out opening 118 for insertion into a medium, such as bone of a patient. Tip 278 can be formed between tabs 236A-236D extending from flexible arms 232A-232D, respectively. Thus, as pin wire 275A or 275B is inserted into shoulder 231 from within lumen 230, flexible arms 232A-232D can flex to permit pin wire 275A or 275B to enter tip 278. Flexible arms 232A-232D can flex over a range of deflections to accommodate pin wires of different sizes, e.g., different diameters.

Driver portion 226 of mobile shaft 221 can have a larger outer diameter than shaft portion 228 so that internal passageway 280 extending through mobile shaft 221 can have a larger diameter within driver portion 226 than shaft portion 228 to, for example, permit flexible arms 232A-232D to deflect outward. Outward deflection of flexible arms 232A-232D via pin wire 275A or 275B can cause flexible arms 232A-232D to apply pressure to pin wire 275A or 275B to retain pin wire 275A or 275B within lumen 230. However, in order to retain pin wire 275A or 275B within lumen 230 so that the pin wire can be advanced and driven into a medium, such as bone, attachment apparatus 210 can be actuated by handle 116 to more firmly grasp the pin wire.

Mobile shaft 221 can be advanced distally to push driver portion 226 into contact with shoulder 231 of flexible collet 222. In particular bearings 224A 224D can be pushed to engage contact surfaces 282A-282D (only contact surfaces 282A and 282C are visible in FIGS. 7A and 7B) of tabs 236A-236D. After initial contact, additional advancement of mobile shaft 221 can cause tabs 236A-236D to deflect radially inward due to the angled nature of contact surfaces 282A-282D. In examples, contact surfaces 282A-282D can have frusto-conical shapes that increase in diameter in the proximal-to-distal direction. As such, the further mobile shaft 221 is advanced, the smaller the diameter of passageway 280 (at contact surfaces 282A-282D) becomes that is engaged with bearings 224A-224D. However, the presence of pin wire 275A or 275B can resist inward flexion of flexible arms 232A-232D. Contact surfaces 282A-282D of tabs 236A-236D and bearings 224A-224D, therefore, form an engagement mechanism that allows flexible arms 232A-232D to push down on pin wire 275A or 275B with sufficient force to immobilize pin wire 275A or 275B when subject to axial loading, such as from a surgeon pushing the pin wire into bone. Angling or ramping of contact surfaces 282A-282D can permit a variable amount of force from driver portion 226 to be applied to pin wires of different sizes depending on the degree to which handle 116 is moved. Shoulder 231 can be shaped to beneficially transfer force from bearings 224A-224D to the pin wire. In the example shown in FIGS. 7A and 7B, tabs 236A-236D have frusto-conical shapes for contact surfaces 282A-282D. Bearings 224A-224D have a radius to distribute forces at the engagement with contact surfaces 282A-282D.

Figure 8:
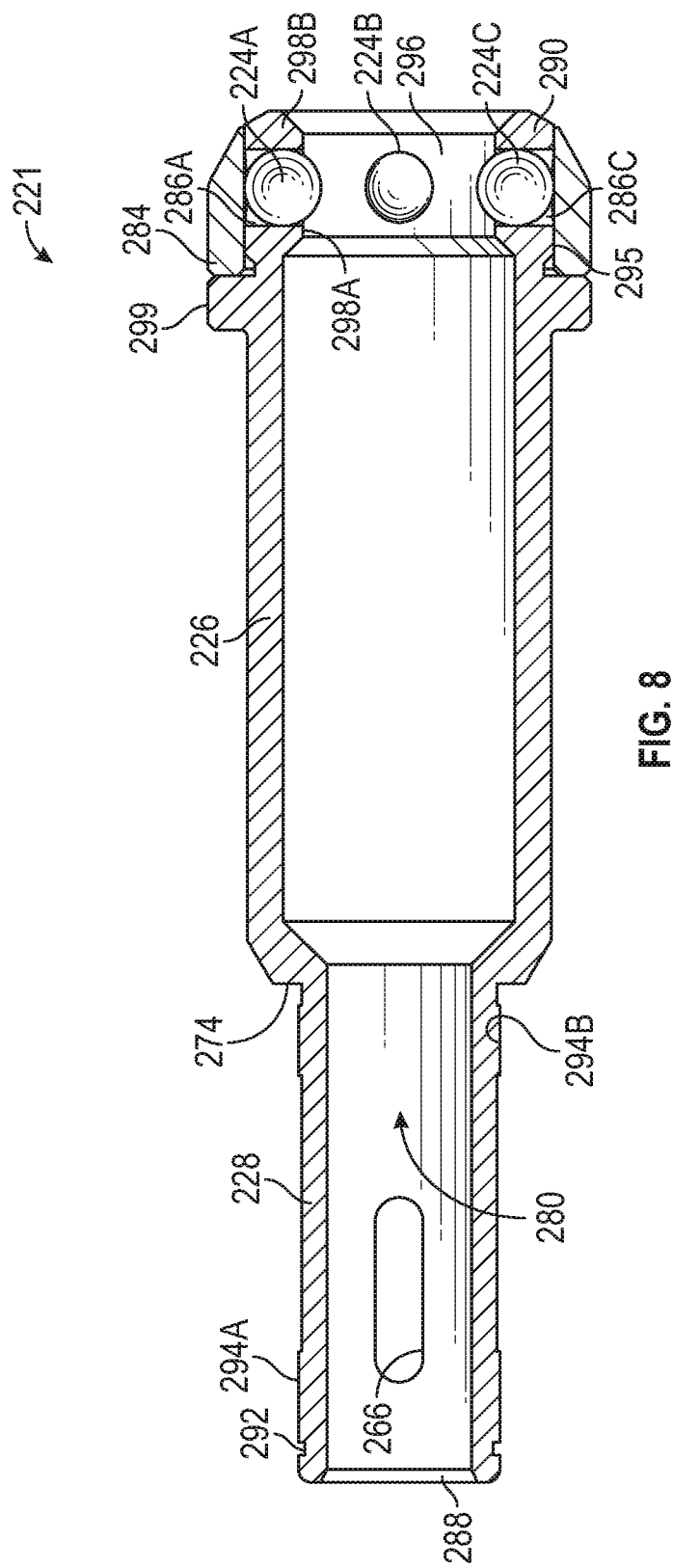
FIG. 8 is a schematic cross-sectional view of the mobile shaft of the attachment apparatus of FIG. 7 showing bearings and a retainer ring.

FIG. 8 is a schematic cross-sectional view of mobile shaft 221 of attachment apparatus 210 of FIG. 7 showing bearings 224A-224D (only bearings 224A 224C are visible in FIG. 8), retainer ring 284 and channels 286A-286D (only channels 286A-286C are visible in FIG. 8). Mobile shaft 221 can extend from proximal end 288 to distal end 290 and internal passageway 280 can extend therethrough. Shaft portion 228 can extend from proximal end 288 to shoulder 274. Driver portion 226 can extend from shoulder 274 to distal end 290. Shaft portion 228 can have an inner diameter configured to receive shaft portion 234 of flexible collet 222 (FIG. 9), and an outer diameter configured to be inserted into bearings 258A and 258B (FIG. 6A). Shaft portion 228 can include groove 292 for receiving lock ring 173A (FIG. 6A), which may comprise a split-ring, that can couple bearings 258A to plunger 140 (FIG. 6A). Shaft portion 228 can include lands 294A and 294B upon which bearings 258A and 258B can be mounted, respectively. Shaft portion 228 can also include opening 266, which can comprise an elongate slot for receiving key 142 (FIG. 6A).

Figure 9:
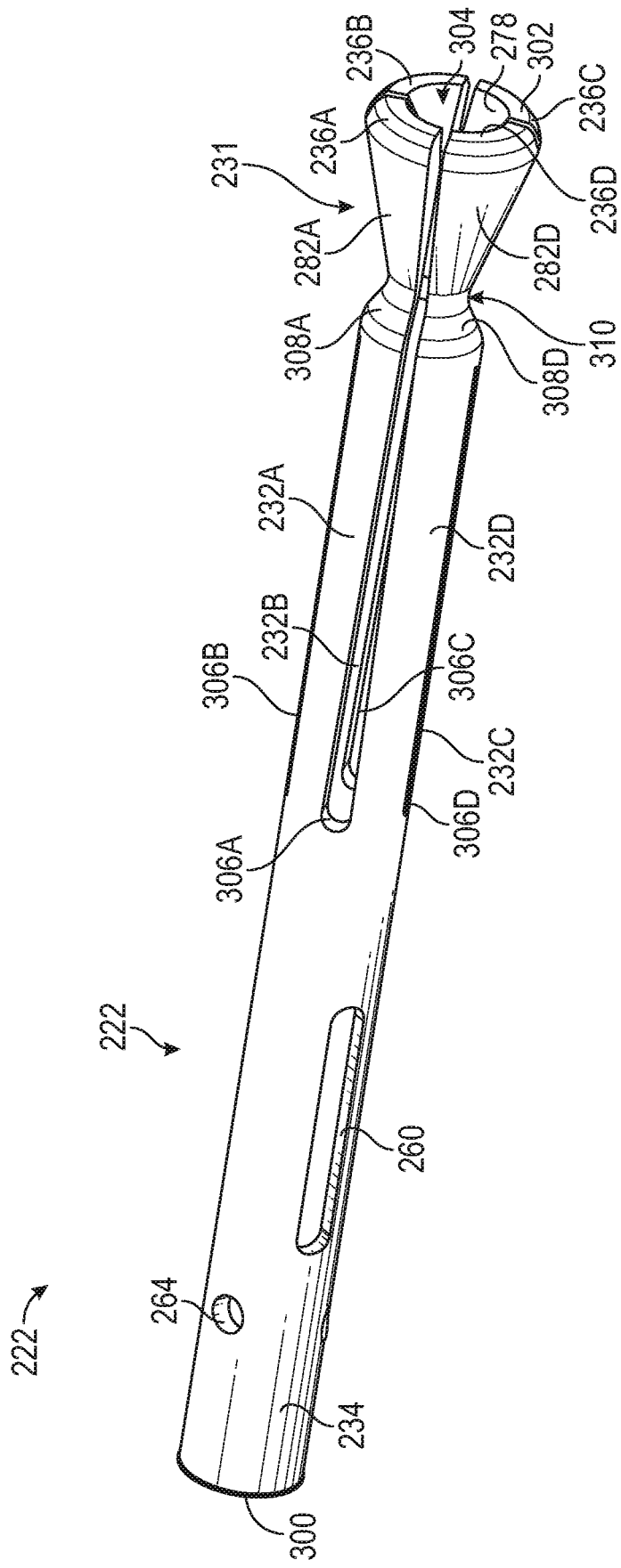
FIG. 9 is a schematic perspective view of the flexible collet of the attachment apparatus of FIG. 7 showing angled contact surfaces connected to flexible arms.

Driver portion 226 can have an outer diameter configured be inserted into nose 114 (FIG. 7A), and an inner diameter configured to receive flexible arms 232A-232D of flexible collet 222 (FIG. 9). The inner diameter of driver portion 226 can be larger than the largest diameter of flexible arms 232A 232B when flexible arms 232A 232B are expanded to receive pin wires. Thus, internal passageway 280 provides clearance for the expansion of flexible arms 232A-232D within driver portion 226, but internal passageway 280 has a smaller diameter in shaft portion 228 so that shaft portion 228 can slide co-axially along shaft portion 234 of flexible collet 222.

Internal passage 280 also includes channels 286A-286D near distal end 290. Channels 286A-286D are constructed similarly as constricted bores that penetrate into driver portion 226 at shelf 295. Only the construction of channel 286A is described herein. Channel 286A can be formed into land 296 in internal passageway 280. Land 296 can orient passageway 280 to be approximately parallel to contact surfaces 282A-282D of shoulder 231 (FIG. 7A). Channel 286A can be configured to be approximately perpendicular to the surface of land 296 at internal passageway 280 so that bearing 224A can be configured to move within channel 286A perpendicularly to contact surfaces 282A. Channel 286A can include flanges 298A and 298B at passageway 280 to retain bearing 224A within channel 286A. Flanges 298A and 298B can restrict channel 286A at passageway 280. Flanges 298A and 298B can each have an axially extending portion so that each at least partially overhangs channel 286A to prevent bearing 224A from passing through channel 286A. Flanges 298A and 298B provide a radially inner limiter for movement of bearing 224A within channel 286A. As shown in FIG. 8, flanges 298A and 298B can comprise opposing portions of a ring-shaped flange. Retainer ring 284 can couple to driver portion 226 to provide a radially outer limiter for movement of bearing 224A within channel 286A. Driver portion 226 can include shelf 295 and flange 299 at distal end 290 to receive retainer ring 284. Shelf 295 provides a portion of mobile shaft 221 that can form an interference fit with retainer ring 284. Flange 299 can prevent retainer ring 284 from sliding along mobile shaft 221 toward proximal end 288. Land 296 can have a thickness such that flanges 298A and 298B and retainer ring 284 can allow bearing 224A to have some play between flanges 298A and 298B and retainer ring 284. In an example, there is approximately 0.005 inch (0.127 mm) radial tolerance for bearing 224A within channel 286A to permit radial displacement of bearing 224A. In other examples, larger tolerances can be used to permit bearing 224A to have a larger displacement. Thus, bearing 224A is free within channels 286A to roll along contact surface 282A (FIG. 7A) as mobile shaft 221 advances toward shoulder 231. Likewise, bearing 224A can retract away from contact surface 282A to facilitate withdrawal of mobile shaft 221 from shoulder 231.

FIG. 9 is a schematic perspective view of flexible collet 222 of attachment apparatus 210 of FIG. 7 showing contact surfaces 282A-282D (only contact surfaces 282A and 282D are shown in FIG. 9) connected to flexible arms 232A 232D (only flexible arms 232A and 232D are shown in FIG. 9).

Flexible collet 222 can extend from proximal end 300 to distal end 302 and internal passageway 304 can extend therethrough. Shaft portion 234 can extend from proximal end 300 to the base of slots 306A-306D. Flexible arms 232A 232D can extend from the base of slots 306A-306D to distal end 302. Shaft portion 234 can have an inner diameter configured to receive pin wires of various sizes, e.g., diameters, and an outer diameter configured to be inserted into shaft portion 228 of mobile shaft 221 (FIG. 8). Shaft portion 234 can include bore 264 to receive a pin for coupling to hub 144 (FIG. 6A). Shaft portion 234 can also include opening 260, which can comprise an elongate slot for receiving key 142 (FIG. 6A).

Flexible arms 232A-232D can have an outer diameter configured be inserted into passageway 280 within driver portion 226 of mobile shaft 221 (FIG. 8), and an inner diameter configured to receive pin wires of various sizes, e.g., diameters. Flexible arms 232A-232D can be biased radially inward so that flexible arms 232A-232D can deflect against the smallest sized pin wired configured to be used with attachment apparatus 210.

Flexible arms 232A-232D can include tapers 308A 308D (only tapers 308A and 308D are visible in FIG. 9) that form valley 310 proximate shoulder 231. The inner diameter of shaft portion 234 and flexible arms 232A-232D can be the same from proximal end 300 up to valley 300. Shoulder 231 can extend from valley 310 at an outward angle to form frusto-conical contact surfaces 282A-282D. Valley 310 forms a reduction in the outer diameter of flexible arms 232A-232D that permits bearings 224A-224D to be freely disengaged from flexible collet 222 when mobile shaft 221 is in a fully retracted position. Frusto-conical contact surfaces 282A-282D allow bearings 224A-224D to gradually engage shoulder 231 for a variety of sized pin wires. As discussed herein, engagement of bearings 224A-224D with frusto-conical contact surfaces 282A-282D can prevent galling between flexible collet 222 and mobile shaft 221 that can arise, particularly in embodiments where mobile shaft 221 can be left to freely rotate about flexible collet 222.

Figure 10:
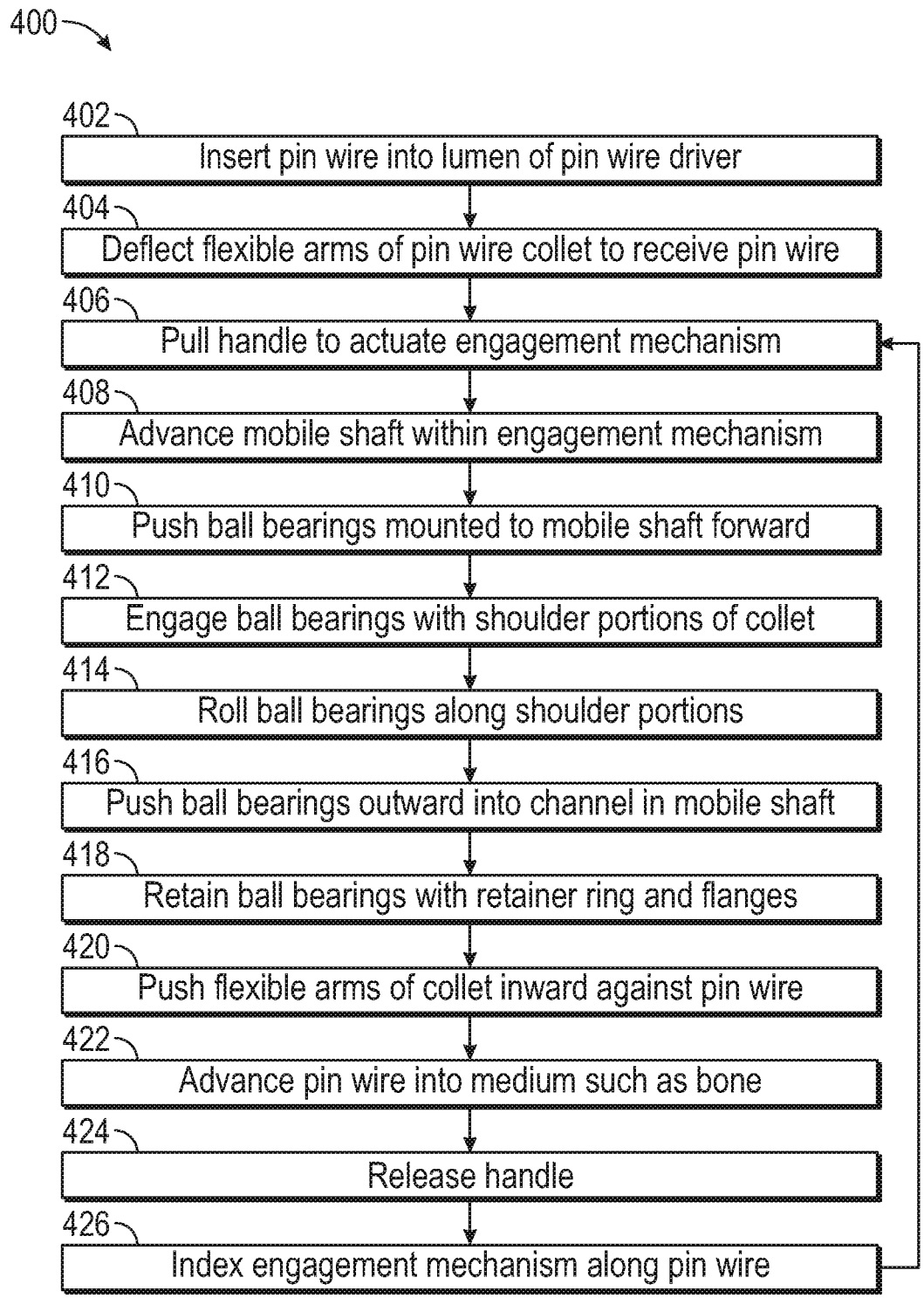
FIG. 10 is a schematic flow diagram of a method of using an illustrative attachment apparatus, such as those described in FIGS. 6A 7B, for driving pin wires according to aspects of the disclosure.

FIG. 10 is a schematic flow diagram of method 400 of using attachment apparatus 210 of FIGS. 7A and 7B for driving pin wires according to aspects of the disclosure. At step 402, a pin wire, such as pin wire 275B of FIG. 7B, can be inserted into lumen 230 of pin wire driver 24 (FIG. 2). For example, pin wire 275B can be inserted into opening 176 in body 112.

At step 404 flexible arms 232A-232D can be deflected to receive pin wire 275B. For example, pin wire 275B can be advanced into the inner diameter portion of flexible collet 222, through body 112 and housing 138, to enter tip passage 178 in shoulder 131. Pin wire 275B can push tabs 236A-236D radially outward to deflect flexible arms 232A-232D. Thus, flexible arms 232A-232D can retain pin wire 275B.

At step 406, handle 116 can be pulled to actuate attachment apparatus 210. As discussed, handle 116 can advance plunger 140 to actuate the engagement mechanism formed by bearings 224A-224D and contact surfaces 282A-282D.

At step 408, mobile shaft 221 can be advanced into engagement with flexible collet 222 at the engagement mechanism.

At step 410, ball bearings 224A-224D that are mounted to mobile shaft 221 can be pushed forward toward contact surfaces 282A-282D.

At step 412, ball bearings 224A-224D can be advanced to engage contact surfaces 282A-282D of shoulder 231 on flexible collet 222.

At step 414, ball bearings 224A-224D can be rolled along contact surfaces 282A-282D. Because ball bearings 224A-224D are free within channels 286A 286D, bearings 224A-224D can roll over a short distance as contact surfaces 282A-282D become engaged with bearings 224A-224D.

At step 416, ball bearings 224A-224D can be pushed radially outward in channels 286A-286D by contact surfaces 282A-282D.

At step 418, ball bearings 224A-224D can be retained within channels 286A-286D by retainer ring 284. Thus, ball bearings 224A-224D can be pushed into engagement with retainer ring 284 as contact surfaces 282A-282D become engaged with bearings 224A-224D. Likewise, flanges 298A and 298B can prevent bearings 224A-224D from passing through channels 286A-286D.

At step 420, as contact surfaces 282A-282D become fully engaged with bearings 224A-224D, bearings 224A-224D can push radially inward toward pin wire 275B against flexible arms 232A-232D. In particular, tabs 236A-236D at shoulder 231 can push against pin wire 275B, with can resist radially inward deflection of flexible arms 232A-232D.

At step 422, pin wire 275B can be advanced into a medium, such as bone. With handle 116 being held in a retracted position, such as by a surgeon, pin wire driver 24 can be pushed into the medium. Because the engagement mechanism of attachment apparatus 210 can immobilize pin wire 275B within lumen 230, pin wire 275B will also be advanced in the direction pin wire driver 24 is pushed by frictional engagement of retention ring 284 with bearings 224A-224D, frictional engagement of bearings 224A-224D with tabs 236A-236D, and frictional engagement of tabs 236A-236D with pin wire 275A.

At step 424, handle 116 can be released to remove the frictional engagement of bearings 224A-224D with tabs 236A-236D. As this occurs, because ball bearings 224A-224D are free within channels 286A-286D, bearings 224A 224D can roll down contact surfaces 282A-282D. Likewise, ball bearings 224A 224D can move radially outward in channels 286A-286D. This rolling motion and radial movement of bearings 224A-224D can help in preventing bearings 224A 224D from becoming stuck against contact surfaces 282A-282D, such as from galling. As mobile shaft 221 moves away from shoulder 231, flanges 298A and 298B can prevent bearings 224A-224D from passing through channels 286A 286D.

At step 426, pin wire driver 24 can be pulled proximally away from the medium into which pin wire 275B is inserted to index the engagement mechanism. The frictional engagement between pin wire 275B and the medium can hold pin wire 275B while movement of pin wire driver 24 from a surgeon can pull pin wire 275B distally through lumen 230. Thus, a different segment of pin wire 725B can be positioned against bearings 224A-224D and contact surfaces 282A-282D of the engagement mechanism. Thus, the process can be repeated again by returning to step 406 to advance pin wire 275B further into the medium.

The attachment apparatuses, engagement mechanisms, mobile shafts, collets, bearings, shoulders, flexible collets and other features described herein can facilitate improved engagement and disengagement of a pin wire driver from a pin wire. The present disclosure provides engagement mechanisms that can include angled contact surfaces that can allow various surfaces within an attachment apparatus to gradually engage and disengage from each other and that can distribute forces within the attachment apparatus. The engagement mechanisms can comprise bearings that engage the angled contact surface. Such engagement mechanisms can prevent attachment apparatuses of pin wire drivers from seizing-up or binding from various causes, such as from galling.

Various Notes & Examples

Example 1 can include or use subject matter such as an engagement mechanism for a driver instrument, the engagement mechanism can comprise: a mobile shaft extending along an axis, the mobile shaft can comprise: a first shaft portion located at a proximal end of the mobile shaft; a driver portion located at a distal end of the mobile shaft; and an internal passageway extending from the proximal end to the distal end; a collet for coupling to a drive input of the driver instrument, the collet can comprise: a second shaft portion disposed within the passageway at the first shaft portion; and flexible arms extending from the second shaft portion within the driver portion; and an angled engagement interface between the driver portion and the flexible arms configured to permit the driver portion to push the flexible arms radially inward when the first shaft portion is slid along the second shaft portion.

Example 2 can include, or can optionally be combined with the subject matter of Example 1, to optionally include an angled engagement interface that can comprise: a plurality of tabs connected to distal ends of the flexible arms to form a cylindrical shoulder; and a frusto-conical surface forming a portion of the passageway at the driver portion; wherein the frusto-conical surface can be advanced to engage the cylindrical shoulder to deflect the flexible arms.

Example 3 can include, or can optionally be combined with the subject matter of Example 1, to optionally include an angled engagement interface that can comprise: a plurality of ramped surfaces extending from distal ends of the flexible arms to form a frusto-conical shoulder; and a plurality of bearings mounted to the passageway at the driver portion; wherein the plurality of bearings can be advanced to engage the frusto-conical shoulder to deflect the flexible arms.

Example 4 can include, or can optionally be combined with the subject matter of one or any combination of Examples 2 or 3 to optionally include a passageway that has a larger diameter in the driver portion than in the first shaft portion.

Example 5 can include, or can optionally be combined with the subject matter of one or any combination of Examples 2 through 4 to optionally include a mobile shaft that can comprise channels extending into the driver portion within the passageway, the plurality of bearings being located in the channels.

Example 6 can include, or can optionally be combined with the subject matter of one or any combination of Examples 2 through 5 to optionally include a mobile shaft that can further comprise a retainer ring coupled to an exterior of the driver portion adjacent the channels.

Example 7 can include, or can optionally be combined with the subject matter of one or any combination of Examples 2 through 6 to optionally include channels that can further comprise opposed flanges to retain the plurality of bearings opposite the retainer ring.

Example 8 can include, or can optionally be combined with the subject matter of one or any combination of Examples 2 through 7 to optionally include opposed flanges that can permit the plurality of bearings to travel radially within the channels.

Example 9 can include, or can optionally be combined with the subject matter of one or any combination of Examples 2 through 8 to optionally include channels that can be angled toward the frusto-conical shoulder.

Example 10 can include, or can optionally be combined with the subject matter of one or any combination of Examples 1 through 9 to optionally include a key rotatably connecting the first shaft portion and the second shaft portion, the key permitting the first shaft portion to slide along the second shaft portion.

Example 11 can include or use subject matter such as a driver instrument that can comprise: a body having an interior; a drive input located at least partially within the interior; a collet coupled to the drive input, the collet can comprise: flexible arms extending in an axial direction; and shoulder portions connected to distal ends of the flexible arms; a mobile shaft disposed at least partially concentrically around the collet, the mobile shaft that can comprise: a first shaft portion engaged with the collet; and a driver portion positioned at a distal end of the first shaft portion to surround the flexible arms; a plurality of bearings mounted to the driver portion to selectively contact the shoulder portions; and a handle mechanism engageable with the first shaft portion of the mobile shaft to translate the mobile shaft along the collet to selectively engage the plurality of bearings with the shoulder portions.

Example 12 can include, or can optionally be combined with the subject matter of Example 11, to optionally include a mobile shaft that can further comprise: a central passage extending through the driver portion and the first shaft portion; wherein the central passage has a larger diameter in the driver portion than in the first shaft portion.

Example 13 can include, or can optionally be combined with the subject matter of one or any combination of Examples 11 or 12 to optionally include a mobile shaft that can comprise radial channels extending into the driver portion within the central passage, the plurality bearings located in the radial channels.

Example 14 can include, or can optionally be combined with the subject matter of one or any combination of Examples 11 through 13 to optionally include a driver portion that can further comprise a retainer ring coupled to an exterior of the driver portion adjacent the radial channels.

Example 15 can include, or can optionally be combined with the subject matter of one or any combination of Examples 11 through 14 to optionally include radial channels that can each further comprise opposed flanges to retain the plurality of bearings opposite the retainer ring.

Example 16 can include, or can optionally be combined with the subject matter of one or any combination of Examples 11 through 15 to optionally include opposed flanges that can permit the plurality of bearing to travel radially within the radial channels.

Example 17 can include, or can optionally be combined with the subject matter of one or any combination of Examples 11 through 16 to optionally include shoulder portions that can comprise: frusto-conical surfaces extending from each of the plurality of flexible arms.

Example 18 can include, or can optionally be combined with the subject matter of one or any combination of Examples 11 through 17 to optionally include radial channels that can be angled toward the frusto-conical surfaces of the shoulder portions.

Example 19 can include, or can optionally be combined with the subject matter of one or any combination of Examples 11 through 18 to optionally include a collet that can further comprise: a second shaft portion from which the plurality of flexible arms extend, the second shaft portion being engaged with the drive input and inserted into the first shaft portion of the mobile shaft.

Example 20 can include, or can optionally be combined with the subject matter of one or any combination of Examples 11 through 19 to optionally include a collet that can further comprise: a plurality of slots disposed between adjacent flexible arms of the plurality of flexible arms.

Example 21 can include, or can optionally be combined with the subject matter of one or any combination of Examples 11 through 20 to optionally include a collet that can further comprise a first elongate opening in the second shaft portion; a mobile shaft that can further comprise a second elongate opening facing the first elongate opening; and an engagement mechanism that can further comprise a key connecting the first elongate opening and the second elongate opening.

Example 22 can include or use subject matter such as a method of advancing a pin wire using a pin wire driver, the method can comprise: inserting a pin wire into a lumen of the pin wire driver; pulling a handle to actuate an engagement mechanism of the pin wire driver; advancing a mobile shaft within the engagement mechanism with the handle; pushing bearings mounted to the mobile shaft axially forward; engaging the bearings with shoulder portions of a pin wire collet; pushing flexible arms connected to the shoulder portions radially inward with the bearings to clamp onto the pin wire; and advancing the pin wire.

Example 23 can include, or can optionally be combined with the subject matter of Example 22, to optionally include releasing the handle; indexing the engagement mechanism along the pin wire; pulling the handle; and advancing the pin wire.

Example 24 can include, or can optionally be combined with the subject matter of one or any combination of Examples 22 or 23 to optionally include shoulder portions that can comprise frusto-conical surfaces of the flexible arms.

Example 25 can include, or can optionally be combined with the subject matter of one or any combination of Examples 22 through 24 to optionally include rolling the bearings along the shoulder portions within channels in the mobile shaft.

Example 26 can include, or can optionally be combined with the subject matter of one or any combination of Examples 22 through 25 to optionally include pushing the bearings radially outward within the channels using the shoulder portions when the bearings engage the shoulder portions.

Example 27 can include, or can optionally be combined with the subject matter of one or any combination of Examples 22 through 26 to optionally include retaining the bearings within a first side of the channels with a retainer ring; and retaining the bearings within a second side of the channels with constrictions of the channels.

Example 28 can include, or can optionally be combined with the subject matter of one or any combination of Examples 22 through 27 to optionally include deflecting the flexible arms outward to insert the pin wire into the pin wire collet.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

The claimed invention is:

1. An engagement mechanism for a driver instrument, the engagement mechanism comprising:
   a mobile shaft extending along an axis, the mobile shaft comprising:
      a first shaft portion located at a proximal end of the mobile shaft;
      a driver portion located at a distal end of the mobile shaft;
      an internal passageway extending from the proximal end to the distal end; and
      channels extending into the driver portion within the internal passageway;
   a collet for coupling to a drive input of the driver instrument, the collet comprising:
      a second shaft portion disposed within the internal passageway at the first shaft portion; and
      flexible arms extending from the second shaft portion within the driver portion; and
   an angled engagement interface between the driver portion and the flexible arms configured to permit the driver portion to push the flexible arms radially inward when the first shaft portion is slid along the second shaft portion, the angled engagement interface comprising:
      a plurality of ramped surfaces extending from distal ends of the flexible arms to form a frusto-conical shoulder; and
      a plurality of bearings positioned within the channels of the driver portion;
   wherein the plurality of bearings can be advanced axially to engage the frusto-conical shoulder to deflect the flexible arms radially; and
   wherein the bearings are configured to roll along the frusta-conical shoulder.

2. The engagement mechanism of claim 1, wherein the passageway has a larger diameter in the driver portion than in the first shaft portion.

3. The engagement mechanism of claim 1, wherein the mobile shaft further comprises a retainer ring coupled to an exterior of the driver portion adjacent the channels.

4. The engagement mechanism of claim 3, wherein the channels further comprise opposed flanges to retain the plurality of bearings opposite the retainer ring.

5. The engagement mechanism of claim 4, wherein the opposed flanges permit the plurality of bearings to travel radially within the channels.

6. The engagement mechanism of claim 1, wherein the channels are angled toward the frusto-conical shoulder.

7. The engagement mechanism of claim 1, further comprising:
   a key rotatably connecting the first shaft portion and the second shaft portion, the key permitting the first shaft portion to slide along the second shaft portion.

8. The engagement mechanism of claim 1, further comprising:
   a body having an interior, wherein the mobile shaft and the collet are rotatably mounted within the body;
   a drive input located at least partially within the interior, the drive input coupled to the collet; and
   a handle mechanism engageable with the first shaft portion of the mobile shaft to translate the mobile shaft along the collet to selectively engage the plurality of bearings with the shoulder portions.

9. The engagement mechanism of claim 8, wherein the internal passageway has a larger diameter in the driver portion than in the first shaft portion.

10. The engagement mechanism of claim 9, wherein the driver portion further comprises a retainer ling coupled to an exterior of the driver portion adjacent the radial channels.

11. The engagement mechanism of claim 10, wherein the radial channels each further comprises opposed flanges to retain the plurality of bearings opposite the retainer ring.

12. The engagement mechanism of claim 11, wherein the opposed flanges permit the plurality of bearing to travel radially within the radial channels.

13. The engagement mechanism of claim 9, wherein the radial channels are angled toward the frusto-conical surfaces of the shoulder portions.

14. The engagement mechanism of claim 8, wherein the second shall portion is engaged with the drive input and inserted into the first shaft portion of the mobile shaft.

15. The engagement mechanism of claim 14, wherein the collet further comprises:
a plurality of slots disposed between adjacent flexible arms of the flexible arms.
16. The engagement mechanism of claim 14, wherein:
the collet further comprises a first elongate opening in the second shaft portion;
the mobile shaft further comprises a second elongate opening facing the first elongate opening; and
the engagement mechanism further comprising a key connecting the first elongate opening and the second elongate opening.
17. The engagement mechanism of claim 8, wherein the mobile shaft and the collet are axially bounded by the body.
18. The engagement mechanism of claim 8, further comprising a gear set coupled to the collet.
19. The engagement mechanism of claim 8, wherein the mobile shaft is mounted within the body within a plunger supported by the body via bearings, the plunger being actuatable by the handle mechanism.
20. A method of advancing a pin wire using a pin wire driver, the method comprising:
inserting a pin wire into a lumen of the pin wire driver;
pulling a handle to actuate an engagement mechanism of the pin wire driver; advancing a mobile shaft within the engagement mechanism with the handle, the mobile shaft comprising a first shaft portion located at a proximal end of the mobile shaft, a driver portion located at a distal end of the mobile shaft, and an internal passageway and channels extending into the driver portion with the internal passageway;
pushing bearings mounted to the mobile shaft within channels axially forward;
engaging the bearings with shoulder portions of a pin wire collet, the pin wire collet comprising a second shaft portion located in the internal passageway and flexible arms having ramped surfaces that form a frusto-conical shoulder such that the bearings can roll along the frusto-conical shoulder;
deflecting the flexible arms connected to the shoulder portions radially inward with the bearings to clamp onto the pin wire, the driver portion and the flexible arms forming an angle engagement interface; and
advancing the pin wire.
21. The method of claim 20, further comprising:
releasing the handle;
indexing the engagement mechanism along the pin wire;
pulling the handle; and
advancing the pin wire.
22. The method of claim 20, wherein the shoulder portions comprise the frusto-conical surfaces of the flexible arms.
23. The method of claim 20, further comprising:
rolling the bearings along the shoulder portions within channels in the mobile shaft.
24. The method of claim 23, further comprising:
pushing the bearings radially outward within the channels using the shoulder portions when the beatings engage the shoulder portions.
25. The method of claim 24, further comprising:
retaining the bearings within a first side of the channels with a retainer ring; and
retaining the bearings within a second side of the channels with constrictions of the channels.
26. The method of claim 20, further comprising:
deflecting the flexible arms outward to insert the pin wire into the pin wire collet.

27. An engagement mechanism for a driver instrument, the engagement mechanism comprising:
a mobile shaft extending along an axis, the mobile shaft comprising:
first shaft portion located at a proximal end of the mobile shaft;
a driver portion located at a distal end of the mobile shaft;
an internal passageway extending from the proximal end to the distal end; and
a first elongate opening in the first shaft portion;
a collet for coupling to a drive input of the driver instrument, the collet comprising:
a second shaft portion disposed within the passageway at the first shaft portion;
flexible arms extending from the second shaft portion within the driver portion; and
a second elongate opening in the second shaft portion, the second elongate opening facing the first elongate opening;
an angled engagement interface between the driver portion and the flexible arms configured to permit the driver portion to push the flexible arms radially inward when the first shaft portion is slid along the second shaft portion;
a key connecting the first elongate opening and the second elongate opening;
a body having an interior;
a drive input located at least partially within the interior, the drive input coupled to the collet;
a plurality of bearings mounted to the driver portion to selectively contact shoulder portions of the collet connected to distal ends of the flexible arms; and
a handle mechanism engageable with the first shaft portion of the mobile shaft to translate the mobile shaft along the collet to selectively engage the plurality of bearings with the shoulder portions;
wherein the second shaft portion is engaged with the drive input and inserted into the first shaft portion of the mobile shaft.
28. An engagement mechanism for a driver instrument, the engagement mechanism comprising:
a mobile shaft extending along an axis, the mobile shaft comprising:
a first shaft portion located at a proximal end of the mobile shaft;
a driver portion located at a distal end of the mobile shaft;
an internal passageway extending from the proximal end to the distal end; and
channels extending into the driver portion within the passageways;
a collet for coupling to a drive input of the driver instrument, the collet comprising:
a second shaft portion disposed within the passageway at the first shaft portion; and
flexible arms extending from the second shaft portion within the driver portion;
an angled engagement interface between the driver portion and the flexible arms configured to permit the driver portion to push the flexible arms radially inward when the first shaft portion is slid along the second shaft portion, the angled engagement interface comprising:
a plurality of ramped surfaces extending from distal ends of the flexible arms to form a frusto-conical shoulder; and a plurality of bearings positioned within the channels of the driver portion;
a body having an interior, wherein the mobile shaft and the collet are rotatably mounted within the body;
a drive input located at least partially within the interior, the drive input coupled to the collet;
a handle mechanism engageable with the first shaft portion of the mobile shaft to translate the mobile shaft along the collet to selectively engage the plurality of bearings with the shoulder portions; and
a gear set coupled to the collet;
wherein the plurality of bearings can be advanced axially to engage the frusto-conical shoulder to deflect the flexible arms radially.

* * * * *

UNITED STATES PATENT AND TRADEMARK OFFICE
CERTIFICATE OF CORRECTION

| | |
|---|---|
| PATENT NO. | : 11,678,893 B2 |
| APPLICATION NO. | : 16/481285 |
| DATED | : June 20, 2023 |
| INVENTOR(S) | : Mark Mahaffey |

It is certified that error appears in the above-identified patent and that said Letters Patent is hereby corrected as shown below:

On the Title Page

In Item (57), in "Abstract", in Column 2, Line 5, after "of," delete "ON"

In Item (57), in "Abstract", in Column 2, Line 9, after "at", delete "co"

In the Claims

In Column 24, Line 20, in Claim 1, delete "frusta-conical" and insert --frusto-conical-- therefor In Column 24, Line 54, in Claim 10, delete "ling" and insert --ring-- therefor In Column 24, Line 66, in Claim 14, delete "shall" and insert --shaft-- therefor In Column 25, Line 25, in Claim 20, after "driver;", insert a linebreak In Column 25, Line 58, in Claim 24, delete "beatings" and insert --bearings-- therefor In Column 26, Line 5, in Claim 27, before "first", insert --a--

Signed and Sealed this
Twenty-fifth Day of July, 2023

Katherine Kelly Vidal
*Director of the United States Patent and Trademark Office*